(12) United States Patent
Park et al.

(10) Patent No.: US 8,865,871 B2
(45) Date of Patent: Oct. 21, 2014

(54) ANTIBODIES AND KITS FOR IMMUNODETECTION OF EPITOPE TAGS

(75) Inventors: Chae Gyu Park, New York, NY (US); Ralph M. Steinman, Westport, CT (US)

(73) Assignee: The Rockefeller University, New York, NY (US)

( * ) Notice: Subject to any disclaimer, the term of this patent is extended or adjusted under 35 U.S.C. 154(b) by 310 days.

(21) Appl. No.: 13/302,136

(22) Filed: Nov. 22, 2011

(65) Prior Publication Data

US 2012/0070845 A1    Mar. 22, 2012

Related U.S. Application Data

(62) Division of application No. 13/076,678, filed on Mar. 31, 2011, now Pat. No. 8,114,634, which is a division of application No. 11/974,384, filed on Oct. 12, 2007, now Pat. No. 7,943,345.

(51) Int. Cl.
| | | |
|---|---|---|
| *C07K 16/18* | (2006.01) | |
| *C07K 16/42* | (2006.01) | |
| *C07K 16/44* | (2006.01) | |
| *C07K 16/28* | (2006.01) | |
| *C07K 7/06* | (2006.01) | |
| *C07K 7/08* | (2006.01) | |

(52) U.S. Cl.
CPC ......... *C07K 16/2851* (2013.01); *C07K 2317/34* (2013.01); *C07K 2319/00* (2013.01); *C07K 16/44* (2013.01); *C07K 7/06* (2013.01); *C07K 7/08* (2013.01)
USPC ..................................... 530/387.9; 530/387.1

(58) Field of Classification Search
None
See application file for complete search history.

(56) References Cited

U.S. PATENT DOCUMENTS 7,943,345 B2    5/2011    Park et al.

OTHER PUBLICATIONS

Cheong, C. et al Production of monoclonal antibodies that recognize the extracellular domain of mouse langerin/CD207. J. Immunl. Methods 324 (1-2), 48-62(2007).

*Primary Examiner* — Christine J Saoud
(74) *Attorney, Agent, or Firm* — Fox Rothschild LLP; Gerard P. Norton; Jianming Jimmy Hao

(57) ABSTRACT

The instant invention provides antibodies which recognize new epitope tags. Related kits for detecting these epitope tags or fusion proteins having these epitope tags are also provided.

20 Claims, 9 Drawing Sheets

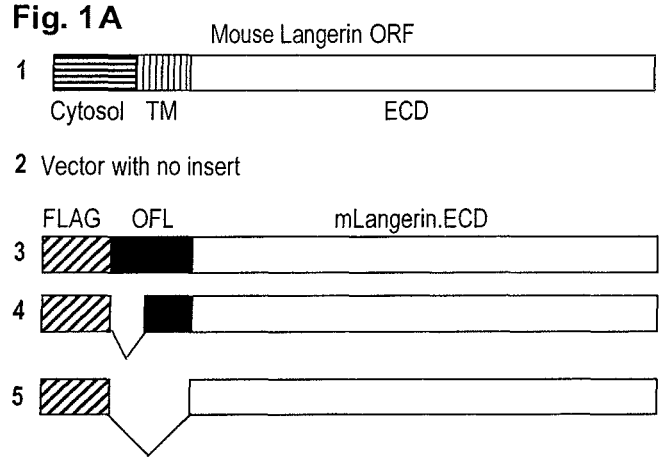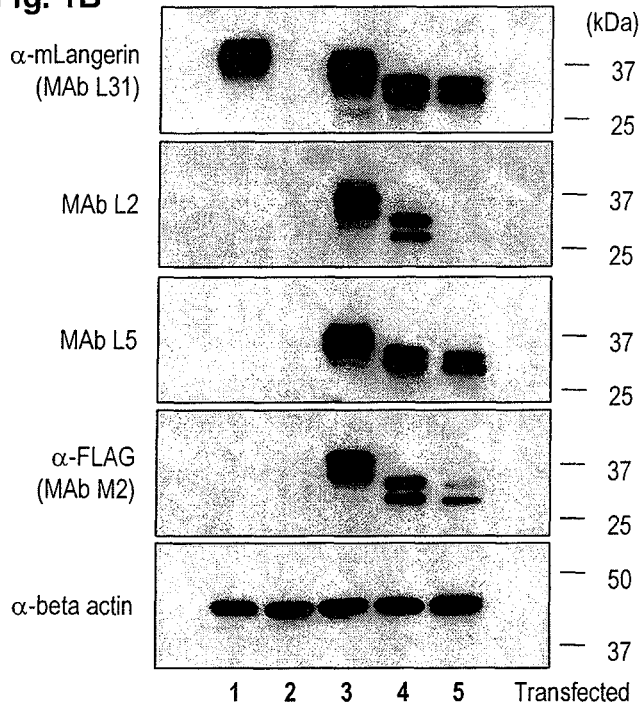

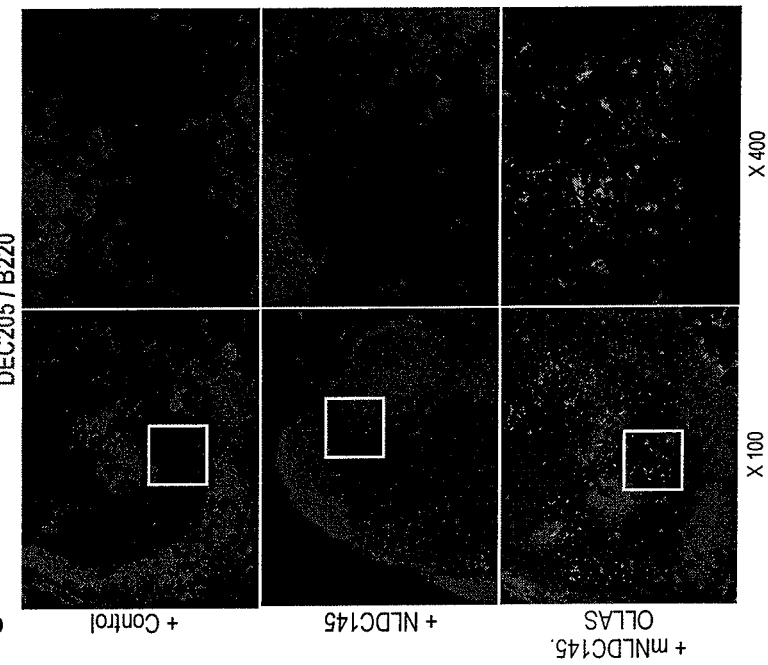
Fig. 7C
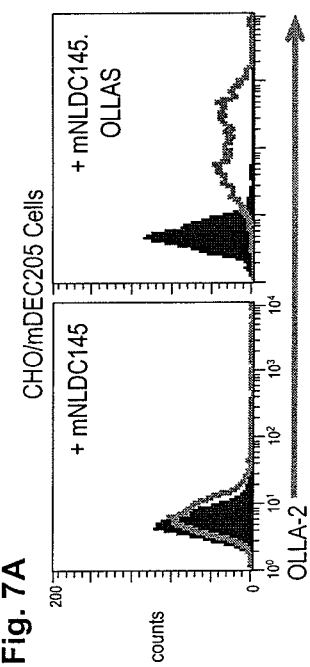
Fig. 7A
Fig. 7B
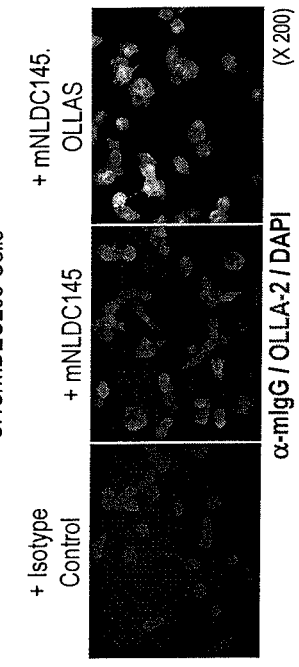

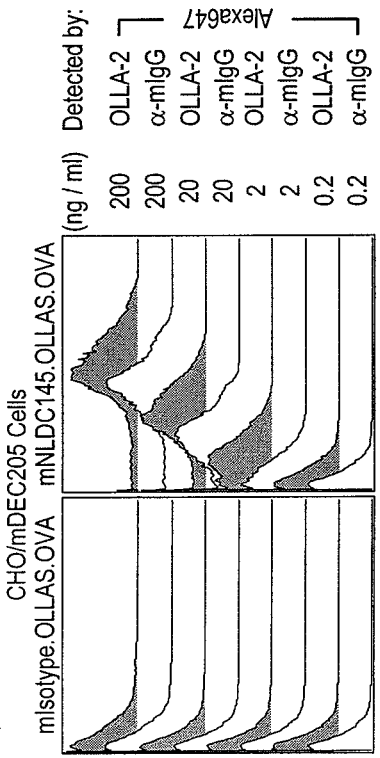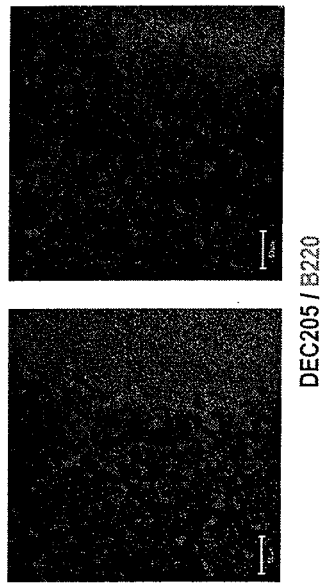
Figure 8

US 8,865,871 B2

ANTIBODIES AND KITS FOR IMMUNODETECTION OF EPITOPE TAGS

CROSS REFERENCE TO RELATED APPLICATIONS

This application is a Divisional of U.S. patent application Ser. No. 13/076,678 filed on Mar. 31, 2011, which application is a Divisional of U.S. patent application Ser. No. 11/974,384 filed on Oct. 12, 2007, the disclosures of which are incorporated herein by reference.

FIELD OF THE INVENTION

This invention relates to methods, systems and reagents for improved immunodetection of expressed recombinant proteins. Specifically this invention relates to the generation of new epitope tags and to the generation of novel antibodies against these epitope tags in addition to already existing epitope tags.

BACKGROUND OF THE INVENTION

Epitope tagging has become an important tool for detecting, localizing and purifying expressed recombinant proteins (Nygren et al., *Trends Biotechnol.* 12: 184-188 (1994)). This methodology involves the fusion of the tag amino acid sequence to the amino or carboxy terminus of a protein of interest, and then identifying the tag with a monoclonal antibody (mAb). For most biochemical applications, the use of epitope tags eliminates the need to generate an antibody to the specific protein that is to be detected and/or purified.

Currently, there are several validated mAb epitopes in wide use for protein tagging, including the FLAG peptide epitope (8 amino acid residues reactive to mAbs M1 and M2) (Hopp et al., *BioTechnology* 6: 1204-1210 (1988)), the V5 epitope (14 amino acids found in the P and V proteins of paramyxovirus, Simian Virus 5) (Southern et al., *J Gen Virol.* 72: 1551-1557 (1991)), the myc epitope (10 amino acids derived from the c-myc proto-oncogen product) (Evan et al., *Mol. Cell. Biol.* 5: 3610-3616 (1985)), the HA epitope (9 amino acids from the hemagglutinin of influenza virus) (Wilson et al., *Cell* 37(3):7 67-778 (1984)), and the 6× His epitope (Lindner et al., *BioTechniques* 22(1): 140-149 (1997)).

However, the choice of an epitope tag depends on the application, because not all tags and in particular the corresponding mAbs are equally suitable for all immunodetection methods, e.g. Western blotting, immunofluorescence staining, immunoprecipitation, and flow cytometry. Accordingly, there is a need in the art for novel detection tags and the antibodies recognizing those detection tags.

SUMMARY OF THE INVENTION

Accordingly, the present invention fulfills this need by providing in one aspect epitope tags and antibodies against these tags. These epitope tags may comprise an amino acid sequence of SEQ ID NO: 1 (SGFANELGPRLMGK). A nucleic acid molecule is also provided wherein the nucleic acid molecule encodes the amino acid SEQ ID NO: 1. In one embodiment, the nucleic acid sequence is identical to SEQ ID NO: 2.

The antibodies selectively bind SEQ ID NO: 1. In addition, antibodies that selectively bind SEQ ID NO: 3 are also provided. Compared to already existing antibodies, the antibodies described herein exhibit an increased affinity to epitope tags comprising SEQ ID NO: 1 and SEQ ID NO: 3. In some embodiments, the antibodies are rat IgG monoclonal antibodies (mAb).

In another aspect, fusion proteins and methods for making these proteins are provided. The fusion proteins comprise an epitope tag comprising an amino acid sequence SEQ ID NO: 1 and an amino acid sequence of a target protein.

In yet another aspect, a method of making a fusion protein comprising SEQ ID NO: 1, and a target protein is provided. The method comprises introducing into a host cell a nucleic acid sequence comprising a first part encoding SEQ ID NO: 1, and a second part encoding the amino acid sequence for the target protein; culturing the host cell under conditions whereby the fusion protein is expressed; isolating the fusion protein by binding the fusion protein to an antibody that binds SEQ ID NO: 1 or SEQ ID NO: 2.

In yet another aspect, kits for diagnostic assays for detecting and analyzing fusion proteins comprising SEQ ID NO: 1, or SEQ ID NO: 3 are provided. These kits may comprise an antibody that binds to SEQ ID NO: 1, or SEQ ID NO: 3, detection means such as another antibody, and, optionally a label.

In another aspect, a cloning vector comprising a nucleic acid sequence encoding SEQ ID NO: 1 is provided. In some embodiment, the nucleic acid sequence comprises SEQ ID NO: 2. The cloning vector may be provided as a kit. Preferably, the kit may also include a OLLAS-tagged control protein construct DNAs.

BRIEF DESCRIPTION OF THE DRAWINGS

FIG. 1A presents a schematic view of different forms of recombinant mouse Langerin (mLangerin) proteins. Newly generated rat IgG monoclonal antibodies (mAbs) recognize tags expressed as fusions with mLangerin. (1) Schematic view of different forms of recombinant mLangerin proteins. Cytosol, transmembrane (TM) and extracellular domain (ECD) of the mLangerin open reading frame (ORF) are indicated. A FLAG epitope tag and/or an *E. coli* OmpF derived flexible linker (OFL) sequences were fused to the N-terminus of the mLangerin ECD. (3-5) Different mLangerin constructs cloned into a CMV mammalian expression vector (2) were transfected into 293T cells, followed by the Western blot analyses with newly generated rat IgG mAbs, i.e. L31 specific for the mLangerin ECD, and the new L2 and L5 MAbs specific for the sequence tags, and anti-FLAG (M2; mouse IgG mAb from Sigma-Aldrich) and anti-beta-actin.

FIG. 1B illustrates results of the Western blot analyses of constructs of FIG. 1A with newly generated rat antibodies.

FIGS. 7A, 7B and 7C present the result of immunodetection of mDEC205 antibodies shown in FIGS. 6A and 6B with OLLAS epitope tag. Immunodetection with OLLAS epitope tag. (7A) Expression vectors for mNLDC145 and mNLDC145.OLLAS as in FIG. 6 were transfected into 293 cells. Stable CHO/mDEC205 cells expressing cell surface mDEC205 were incubated with the culture supernatants containing mNLDC145 (left panel) or mNLDC145.OLLAS (right panel). Then, the cells were further incubated with mAb OLLA-2 followed by PE-conjugated anti-rat IgG prior to flow cytometry. (7B) Stable CHO/mDEC205 cells were immunostained with either mouse control IgG (left panel), mNLDC145 (middle panel), or mNLDC145.OLLAS (right). Then, the cells were probed with anti-mouse IgG, OLLA-2/anti-rat IgG, and DAPI. (7C) Mouse lymph nodes were immunostained with rat control IgG (upper panels), rat IgG mAb NLDC145 (middle panels), and mNLDC145.OLLAS (lower panels). Then, the tissues were stained with mAb OLLA-2 followed by anti-rat IgG labeled with Alexa488 and anti-B220. Insets in left panels are shown at 400 fold magnification in the right.

FIGS. 8A, 8B and 8C present results of immunodetection of engineered mAbs with protein fusion by the use of OLLAS epitope tag/linker and mAb OLLA-2. (8A) Schematic view of engineered mAbs fused with ovalbumin where OLLAS epitope tag was used as a linker. Murinized IgG isotype control mAb, mIsotype.OLLAS.OVA (left), and anti-mDEC205 mAb mNLDC145.OLLAS.OVA (right) are shown. (8B) CHO/mDEC205 cells were incubated for 15 min with 2 μg/ml of mAb mNLDC145.OLLAS.OVA (right panel) or the corresponding isotype control, mIsotype.OLLAS.OVA (left panel). After washing, the cells were incubated with different doses of Alexa647 labeled OLLA-2 or anti-mouse IgG respectively. The analysis was performed by FACS. The data are representative of two experiments. (8C) Mouse lymph nodes were immunostained with rat IgG mAb NLDC145 (left panel) and murinized mAb mNLDC145.OLLAS.OVA (right panel). Then, the tissues were stained with Alexa647 labeled anti-rat IgG (left panel) or Alexa647 labeled OLLA-2 (right panel) and anti-B220. Bar scales equal 50 μm.

DETAILED DESCRIPTION OF THE INVENTION

Figure 2A:
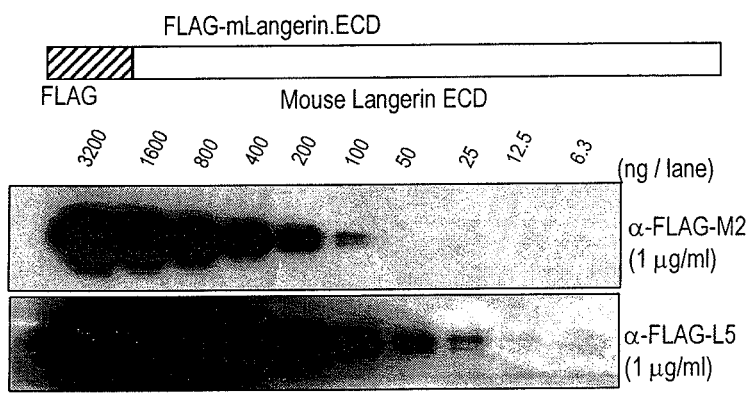
FIGS. 2A, 2B and 2C present results of comparison of binding sensitivity to FLAG epitope tagged proteins between mouse mAb M2 and the new rat mAb L5 under similar conditions. (2A) Purified protein comprised of mLangerin ECD with an N-terminal FLAG tag (structure shown in upper panel) was diluted as indicated and separated in SDS-PAGE gels followed by blotting with 1 µg/ml of mouse anti-FLAG mAb M2 (middle panel) and rat anti-FLAG mAb L5 (lower panel). (2B) 293T cells were transfected with pCMV-FLAG-mSIGN-R1.ECD (structure shown in upper panel), lysed, diluted as indicated, and separated in SDS-PAGE gels followed by blotting with 0.5 µg/ml of mouse anti-FLAG mAb M2 (middle panel) and rat anti-FLAG mAb L5 (lower panel). (2C) 293T cells were transfected with pIRES.Neo3-rP11-FLAG.HA (structure shown in upper panel), lysed, diluted as indicated, and separated in SDS-PAGE gels followed by blotting with 1 µg/ml of mouse anti-FLAG mAb M2 (middle panel) and rat anti-FLAG mAb L5 (lower panel).

Monoclonal antibodies against epitope tags are an efficient, convenient and rapid method for detecting recombinant protein expression (Jarvik and Telmer, *Annu Rev Genet.* 32:601-618 (1998)). If there is no antibody against the protein of interest, adding an epitope tag to this protein allows for protein detection with an antibody against the epitope sequence. Accordingly, in one aspect, novel epitope tags and antibodies against these tags are disclosed.

As used herein, the term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

In one embodiment, the epitope tag may comprise a 14 amino acid sequence presented herein as SEQ ID NO: 1: SGFANELGPRLMGK, which may be referred to as OLLAS. This sequence resides in the junction between a highly flexible domain in *E. coli* OmpF protein, named OFL (OmpF linker), and a mouse Langerin extracellular domain (mLangerin ECD). These epitope tags are referred to herein as OLLAS (*E. coli* OmpF Linker and mouse Langerin fusion Sequence epitope.)

Alternatively, the epitope tag may comprise a fragment of SEQ ID NO: 1. Some suitable examples of fragments include, but are not limited to, an amino acid sequence with up to 4 amino acid deletion or changes at the N-terminal of the amino acid of SEQ ID NO: 1 or an amino acid sequence with up to 2 amino acid deletion or changes at the C-terminal of the amino acid of SEQ ID NO: 1. In different embodiments, the suitable fragment comprises at least one of the following:

| | |
|---|---|
| NELGPRLM | SEQ ID NO: 4 |
| ANELGPRLM | SEQ ID NO: 5 |
| FANELGPRLM | SEQ ID NO: 6 |
| GFANELGPRLM | SEQ ID NO: 7 |
| SGFANELGPRLM | SEQ ID NO: 8 |
| NELGPRLMG | SEQ ID NO: 9 |
| ANELGPRLMG | SEQ ID NO: 10 |
| FANELGPRLMG | SEQ ID NO: 11 |
| GFANELGPRLMG | SEQ ID NO: 12 |
| SGFANELGPRLMG | SEQ ID NO: 13 |
| NELGPRLMGK | SEQ ID NO: 14 |
| ANELGPRLMGK | SEQ ID NO: 15 |
| FANELGPRLMGK | SEQ ID NO: 16 |
| GFANELGPRLMGK | SEQ ID NO: 17 |

In another embodiment, an isolated nucleic acid sequence encoding SEQ ID NO: 1 is provided. One with ordinary skills in the art will undoubtedly understand that different nucleic acid sequences may encode the same amino acid sequence. One example is presented herein as SEQ ID NO: 2: AGT GGC TTT GCG AAT GAA TTG GGA CCT AGG TTG ATG GGC AAG. Furthermore, isolated nucleic acid sequences encoding fragments of SEQ ID NO: 1 are provided. Sequences for different fragments can be easily construed by one with ordinary skill in the art.

The epitope tags of the instant invention and the nucleic acid sequences encoding those epitopes may be obtained by a variety of methods well known in the art. Considering short size of these amino- and nucleic acid sequences, one of the most convenient ways to make these molecules is to order them from suppliers who synthesize short peptides and oligonucleotides. Suitable examples of such companies are Invitrogen, Inc., (Carlsbad Calif.) and The Midland Certified Reagent Company, Inc. (Midland, Tex.).

Antibodies against the OLLAS epitope tags are also provided. Such antibodies, referred to as OLLA-2, selectively bind to SEQ ID NO: 1 and its fragments.

In some embodiments, these antibodies may exhibit an increased affinity to the OLLAS epitope tags compared to other available antibodies and, thus, may enhance the performance of a variety of immunodetection methods, including, but not limited to, Western Blot, immunocytochemistry, immunohistochemistry, flow cytometry, and immunoprecipitation. It has been shown that, by Western blotting, 1 µg/ml of anti-V5 mAB is capable of detecting OLLAS in cell lysates from about 1250 cells transfected with SEQ ID NO: 1 and 0.5 µg/ml of anti-Flag mAB M2 is capable of detecting OLLAS in cell lysates from about 15,000 such cells. Accordingly, preferably OLLA-2 may be capable of detecting less than the amount detected by anti-Flag mAB M2 and anti-V5 mAB. More preferably, about 1 µg/ml of OLLA-2 may be capable of detecting OLLAS from about 10 cells, and 0.5 µg/ml of OLLA-2 may be capable of detecting OLLAS from about 78 of these cells.

In another embodiment, antibodies against a known epitope, FLAG, are provided which are herein referred to as the new anti-FLAG L5. The FLAG epitope comprises an 8 amino acid sequence SEQ ID NO: 3: DYKDDDDK. Preferably, new anti-FLAG L5 is capable of binding to SEQ ID NO: 3 with increased affinity compared to existing antibodies against FLAG, and thus, enhances the performance of a variety of immunodetection methods, including Western Blot, immunocytochemistry, immunohistochemistry, flow cytometry, and immunoprecipitation. In one embodiment, the new anti-FLAG L5 may detect both N-terminal and C-terminal FLAG tagged proteins about 2 to 8 times better than the conventional anti-FLAG mAb M2 using the Western blot analysis. Preferably, in Western blot analysis, 1 mg/ml of new anti-FLAG L5 can detect less than 100 ng of N-terminally FLAG tagged purified protein or lysates from about 2,500 cells transfected with N-terminally FLAG tagged recombinant protein construct, and more preferably it can detect about as little as 25 ng of N-terminally FLAG tagged purified protein or lysates from about 1,250 cells transfected with N-terminally FLAG tagged recombinant protein construct.

OLLA-2 and new anti-FLAG L5 antibodies may take one of many forms known in the art. The term "antibody" is used here in the broadest sense and specifically covers monoclonal antibodies (including full length monoclonal antibodies), polyclonal antibodies, monospecific antibodies, multispecific antibodies (e.g., bispecific antibodies), antibody derivatives, functional equivalents and antibody fragments so long as they retain its antigen binding capability, generally including, but not limited to, the specific binding member or antigen-binding portion. The terms "specific binding member" and "antigen-binding portion" include, but are not limited to, (i) a Fab fragment, a monovalent fragment consisting of the VL, VH, CL and CH domains; (ii) a F(ab')2 fragment, a bivalent fragment comprising two Fab fragments linked by a disulfide bridge at the hinge region; (iii) a Fd fragment consisting of the VH and CH domains; (iv) a Fv fragment consisting of the VL and VH domains of a single arm of an antibody (v) a dAb fragment, which comprises a VH domain; (vi) an isolated complementarily determining region (CDR); (vii) a 'scAb', an antibody fragment containing VH and VL as well as either CL or CH; and (viii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application Publication No. WO 02/32925).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibodies may be generated from different species, including but not limited to, mice, rats, rabbits, or primates.

For example, the monoclonal antibodies to be used in accordance with the methods disclosed herein may be made by the hybridoma method first described by Kohler and Milstein, Nature, 256, 495-497 (1975), which is incorporated herein by reference. Alternatively, the monoclonal antibodies may be made by recombinant DNA methods which are disclosed, for example, in U.S. Pat. No. 4,816,567, which is incorporated herein by reference, and are also generally described below. Finally, techniques are available to the artisan for the selection of antibody fragments from libraries using enrichment technologies, including but not limited to phage display, ribosome display (Hanes and Pluckthun, 1997, Proc. Nat. Acad. Sci. 94: 4937-4942), bacterial display (Georgiou, et al., 1997, Nature Biotechnology 15: 29-34) and/or yeast display (Kieke, et al., 1997, Protein Engineering 10: 1303-1310.)

Beyond species specific monoclonal antibodies described above, the antibodies of the present invention may also be in the form of a "chimeric antibody", a monoclonal antibody constructed from the variable regions derived from say, the murine source, and constant regions derived from the intended host source (e.g., human; for a review, see Morrison and Oi, 1989, Advances in Immunology, 44: 65-92). The variable light and heavy genes from the rodent (e.g., mouse) antibody are cloned into a mammalian expression vector which contains an appropriate human light chain and heavy chain coding region, respectively. These heavy and light "chimeric" expression vectors are cotransfected into a recipient cell line and selected and expanded by known techniques. This cell line may then be subjected to known cell culture techniques, resulting in production of both the light and heavy chains of a chimeric antibody Such chimeric antibodies have historically been shown to have the antigen-binding capacity of the original rodent monoclonal while significantly reducing immunogenicity problems upon host administration.

A logical improvement to the chimeric antibody is the "humanized antibody," which arguably reduces the chance of the patient mounting an immune response against a therapeutic antibody when compared to use of a chimeric or full murine monoclonal antibody The strategy of "humanizing" a murine Mab is based on replacing amino acid residues which differ from those in the human sequences by site directed mutagenesis of individual residues or by grafting of entire complementarily determining regions (Jones et al., 1986, Nature 321: 522-526). This technology is again now well known in the art and is represented by numerous strategies to improve on this technology; namely by implementing strategies including, but not limited to, "reshaping" (see Verhoeyen, et al., 1988, Science 239: 1534-1536), "hyperchimerization" (see Queen, et al., 1991, Proc. Natl. Acad. Sci. 88:2869-2873) or "veneering" (Mark, et al., 1994, Derivation of Therapeutically Active Humanized and Veneered anti-CD18 Antibodies Metcalf end Dalton, eds. Cellular Adhesion: Molecular Definition to Therapeutic Potential. New York: Plenum Press, 291-312). These strategies all involve to some degree sequence comparison between rodent and human sequences to determine whether specific amino acid substitutions from a rodent to human consensus is appropriate. Whatever the variations, the central theme involved in generating a humanized antibody relies on CDR grafting, where these three antigen binding sites from both the light and heavy chain are effectively removed from the rodent expressing antibody clone and subcloned (or "grafted") into an expression vector coding for the framework region of the human antibody. Therefore, a "humanized antibody" is effectively an antibody constructed with only murine CDRs (minus any additional improvements generated by incorporating one or more of the above mentioned strategies), with the remainder of the variable region and all of the constant region being derived from a human source.

Yet another improvement over re-engineered antibodies as reviewed above is the generation of fully human monoclonal antibodies. The first involves the use of genetically engineered mouse strains which possess an immune system whereby the mouse antibody genes have been inactivated and in turn replaced with a repertoire of functional human antibody genes, while leaving other components of the mouse immune system unchanged. Such genetically engineered mice allow for the natural in vivo immune response and affinity maturation process which results in high affinity, fully human monoclonal antibodies This technology is again now well known in the art and is fully detailed in various publications, including but not limited to U.S. Pat. Nos. 5,939,598; 6,075,181; 6,114,598; 6,150,584 and related family members (assigned to Abgenix, disclosing their XenoMouse technology); as well as U.S. Pat. Nos. 5,545,806; 5,569,825; 5,625, 126; 5,633,425; 5,789,650; 5,877, 397; 5,661,016; 5,814, 318; 5,874,299; and 5,770,429 (assigned to GenPharm International and available through Medarex, under the umbrella of the "UltraMab Human Antibody Development System"). See also a review from Kellerman and Green (2002, Curr. Opinion in Biotechnology 13: 593-597).

In the preferred embodiments, the L2 anti-OLLAS antibodies (which may also be referred to as OLLA-2 antibodies) and new anti-FLAG L5 antibodies are rat monoclonal antibodies.

In another aspect, fusion proteins are provided. In one embodiment, the fusion proteins may comprise epitope tags encoded by SEQ ID NO: 1 or its fragments (such as SEQ ID NO: 4-SEQ ID NO: 17), and an amino acid sequence of a target protein. The epitope tags may be connected to the C-terminal, the N-terminal or both N- and C-termini of the target protein. Furthermore, the methods of making such fusion proteins are provided. The methods comprise introducing into a host cell a nucleic acid sequence comprising a first part encoding the epitope tag, and a second part encoding an amino acid sequence for the target protein, culturing the host cell under conditions that promote expression of protein linked to the epitope tag, and isolating the fusion protein.

The term "isolating" or "isolated" is used herein as it is used within the art. It means that antibodies, antibody fragment/specific binding members, nucleic acid molecules, and proteins are free or substantially free of material with which they are naturally associated such as other polypeptides or nucleic acids with which they are found in their natural environment, or the environment in which they are prepared (e.g. cell culture) when such preparation is by recombinant DNA technology (practiced ill vitro) or in vivo. "Isolating" or "isolated" covers any form containing the identified and characterized antibodies, antibody fragments/specific binding members, nucleic acid molecules, proteins described herein following their removal from that initial environment.

Techniques for such manipulations are well known and are readily available to the artisan of ordinary skill in the art. Many treatises on recombinant DNA methods have been published, including Sambrook, et al., Molecular Cloning: A Laboratory Manual, $2^{nd}$ edition, Cold Spring Harbor Press, (1988), Davis, et al., Basic Methods in Molecular Biology, Elsevier (1986), and Ausubel, et al., Current Protocols in Molecular Biology, Wiley Interscience (1988). These reference manuals are specifically incorporated by reference herein in their entirety.

In general, a nucleic acid molecule comprising a sequence encoding an epitope tag and a nucleic acid molecule encoding a target protein may be linked, in whole or in part, to form "recombinant DNA molecules" which encode a desired fusion protein. These recombinant DNA molecules may be prepared using any known technique. For example, the sequences for the eptiope tag and the target protein may be cloned, sequenced and ligated to make the recombinant DNA molecule for the fusion protein. In one embodiment, the sequences may be generated and cloned using the polymerase chain reaction (PCR). Alternatively, a cloning vector comprising of DNA or RNA may be employed. Cloning vectors are defined herein as an agent that can carry and reproduce a DNA fragment into a host cell. For most cloning purposes DNA vectors are preferred. Typical vectors include plasmids, modified viruses, bacteriophage, cosmids, yeast artificial chromosomes, and other forms of episomal or integrated DNA. It is within the purview of the skilled artisan to determine an appropriate vector for a particular gene transfer and generation of a recombinant DNA for a fusion protein or other use.

In one aspect, cloning vectors comprising a nucleic acid sequence encoding SEQ ID NO: 1 are provided. As stated above, cloning vectors are defined herein as agents that can carry and reproduce a DNA fragment into a host cell. In one exemplary embodiment, the nucleic acid sequence may comprise SEQ ID NO: 2. The cloning vector may be prepared by any known technique such as described in reference manuals cited above. The cloning vector may further include a polyadenylation signal, a transcription termination sequence, and a multiple cloning site comprising at least one endonuclease restriction site. The vector may further comprise a promoter. In some embodiments, in the operational vector, the nucleic acid sequence may be located upstream of the polyadenylation signal and the transcription termination sequence, and the at least one endonuclease restriction site may be located upstream of said polyadenylation signal and the transcription termination sequence.

A target nucleic acid sequence may be cloned into the multiple cloning site of the cloning vector. It is preferable that the nucleic acid sequence encoding SEQ ID NO: 1 or its fragments, and the target nucleic acid sequence may be transcribed as a single mRNA and translated into a single amino acid sequence that includes SEQ ID NO: 1 or its fragments. Depending on the desired location of the epitope tag in the fusion protein, the at least one endonuclease restriction site may be located downstream of the nucleic acid sequence encoding SEQ ID NO: 1 or its fragments for N-terminal tagging, or upstream of the nucleic acid sequence encoding SEQ ID NO: 1 or its fragments for C-terminal tagging, or both.

The cloning vector may be provided as a kit. In addition to the cloning vector, the kit may include a forward primer; a reverse primer; a ligase; at least one restriction endonuclease; an aliquote of competent cells; instructions or any combinations thereof. The kit may also include a control. In one exemplary embodiment, the control may be a vector comprising a DNA sequence that encodes a known OLLAS-tagged protein (e.g., a GFP protein).

Once recombinant DNA molecules are prepared, they may be inserted into an expression vector and transfected into a host cell. Methods of subcloning nucleic acid molecules of interest into expression vectors, transforming or transfecting host cells containing the vectors, and methods of making substantially pure protein comprising the steps of introducing the respective expression vector into a host cell, and cultivating the host cell under appropriate conditions are well known. The fusion protein so produced may be harvested from the host cells in conventional ways. Any known expression vector may be utilized to practice this portion of the invention, including any vector containing a suitable promoter and other appropriate transcription regulatory elements. The resulting expression construct is transferred into a prokaryotic or eukaryotic host cell to produce recombinant protein.

Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency.

Commercially available mammalian expression vectors which may be suitable, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNA-Ianp (Invitrogen), pcDNA3 (Invitrogen), pMClneo (Stratagene), pXT1 (Stratagene), pSG5 (Stratagene), EBO pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUC-Tag (ATCC 37460), and 1ZD35 (ATCC 37565). Also, a variety of bacterial expression vectors are available, including but not limited to pCR2.1 (Invitrogen), pET1 la (Novagen), lambda gtl 1 (Invitrogen), and pKK223-3 (Pharmacia). In addition, a variety of fungal cell expression vectors may be used, including but not limited to pYES2 (Invitrogen) and Pichie expression vector (Invitrogen). Also, a variety of insect cell expression vectors may be used, including but are not limited to pBlueBacIII and pBlueBacHis2 (Invitrogen), and pAcG2T (Pharmingen).

Recombinant host cells may be prokaryotic or eukaryotic, including but not limited to, bacteria such as *E. coli*, fungal cells such as yeast, mammalian cells including, but not limited to, cell lines of bovine, porcine, monkey and rodent origin; and insect cells. Mammalian species which may be suitable, include but are not limited to, L cells L-M(TK-) (ATCCCCL1.3), L cells L-M (ATCC CCL 1.2), Saos-2 (ATCCHTB-85), 293 (ATCCCRL1573), Raji (ATCC CCL 86), CV-1 (ATCC CCL 70), COS-1 (ATCC CRL1650), COS-7(ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1(ATCC CCL 26), MRC-5 (ATCCCCL171) and CPAE (ATCC CCL 209).

The fusion proteins of interest may be isolated using any known protein purification technique. Suitable examples include, but are not limited to, immuno-affinity chromatography, affinity chromatography, protein precipitation, buffer exchange, ion exchange chromatography, hydrophobic interaction chromatography, size-exclusion chromatography, electrophoresis or combination thereof. In the preferred embodiment, the fusion protein is isolated using the OLLA-2 or new anti-FLAG L5 antibodies. These antibodies may be dissociated from the fusion protein using any known techniques such as by cleaving the antibody off using a protease or washing the antibody-antigen complex with a solution which favors dissociation of the antigen and the antibody (for example, using the solution of high ionic strength). Many of these techniques are described, for example, in Biochemistry, R. H. Garrett and C. M. Grisham, Suanders College Publishing, (1995); and Molecular and Cell Biology, Third Edition, H Lodish, D. Baltimore, A. Berk, S. L. Zipursky, P. Matsudaira, J. Darnell, Scientific American Books, Inc. (1995), which are incorporated herein by reference.

In yet another aspect, kits for diagnostic assays for detecting and analyzing tagged protein are provided. Such assays may be carried out by any techniques known and available to the artisan, including but not limited to Western blots, ELISAs, radioimmunoassays, immunohistochemical assays, immunoprecipitations, or other immunochemical assays known in the art. These kits may comprise any of the antibodies described above, detection means corresponding to the antibody, and, optionally a label.

The antibodies described herein may be used as the basic reagents in a number of different immunoassays to determine the presence of a protein tagged either with OLLAS or FLAG epitopes in a sample. Generally speaking, the antibodies can be employed in any type of immunoassay, whether qualitative or quantitative. This includes both the two-site sandwich assay and the single site immunoassay of the non-competitive type, as well as in traditional competitive binding assays.

One embodiment of interest, for ease of detection, and its quantitative nature, is the sandwich or double antibody assay, of which a number of variations exist, all of which are intended to be encompassed by this portion of the present invention. For example, in a typical forward sandwich assay, unlabeled antibody is immobilized on a solid substrate, e.g., microtiter plate wells, and the sample to be tested is brought into contact with the bound molecule. After a suitable period of incubation, for a period of time sufficient to allow formation of an antibody-antigen binary complex, a second antibody, labeled with a reporter molecule capable of inducing a detectable signal, is then added and incubation is continued allowing sufficient time for binding with the antigen at a different site and the formation of a ternary complex of antibody-antigen-labeled antibody. Any unreacted material is washed away, and the presence of the antigen is determined by observation of a signal, which may be quantitated by comparison with a control sample containing known amounts of antigen.

Variations on the forward sandwich assay include the simultaneous assay, in which both sample and antibody are added simultaneously to the bound antibody, or a reverse sandwich assay in which the labeled antibody and sample to be tested are first combined, incubated and added to the unlabelled surface bound antibody. These techniques are well known to those skilled in the art, and the possibility of minor variations will be readily apparent. As used herein, "sandwich assay" is intended to encompass all variations on the basic two-site technique.

For the sandwich assays, the only limiting factor is that both antibodies have different binding specificities for the OLLAS or FLAG epitopes. Thus, a number of possible combinations are possible. As a more specific example, in a typical forward sandwich assay, a primary antibody is either covalently or passively bound to a solid support. The solid surface is usually glass or a polymer, the most commonly used polymers being cellulose, polyacrylamide, nylon, polystyrene, polyvinylchloride or polypropylene. The solid supports may be in the form of tubes, beads, discs or microplates, or any other surfaces suitable for conducting an immunoassay. The binding processes are well known in the art. Following binding, the solid phase-antibody complex is washed in preparation for the test sample. An aliquot of the sample containing a protein tagged with either OLLAS or FLAG epitope to be tested is then added to the solid phase complex and incubated at 25° C. for a period of time sufficient to allow binding of any tagged proteins present to the antibody specific for that tag. The second antibody is then added to the solid phase complex and incubated at 25° C. for an additional period of time sufficient to allow the second antibody to bind to the primary antibody-antigen solid phase complex. The second antibody may be linked to a reporter molecule, the visible signal of which is used to indicate the binding of the second antibody to any antigen in the sample. By "reporter molecule", as used in the present specification is meant a molecule which by its chemical nature, provides an analytically detectable signal which allows the detection of antigen-bound antibody. Detection must be at least relatively quantifiable, to allow determination of the amount of antigen in the sample, this may be calculated in absolute terms, or may be done in comparison with a standard (or series of standards) containing a known normal level of antigen.

The most commonly used reporter molecules in this type of assay are either enzymes or fluorophores. In the case of an enzyme immunoassay an enzyme is conjugated to the second antibody, often by means of glutaraldehyde or periodate. As will be readily recognized, however, a wide variety of different conjugation techniques exist, which are well known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-antigen complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantitated, usually spectrophotometrically, to give an evaluation of the amount of antigen that is present in the serum sample.

Additionally, fluorescent compounds, such as fluorescein or rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in the enzyme immunoassay (EIA), the fluorescent-labeled antibody is allowed to bind to the first antibody-tagged protein complex. After washing the unbound reagent, the remaining ternary complex is then exposed to light of the appropriate wavelength, and the fluorescence observed indicates the presence of the antigen. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

In another embodiment, the sample to be tested may be used in a single site immunoassay wherein it is adhered to a solid substrate either covalently or noncovalently. An unlabeled anti-OLLAS or anti-FLAG antibody is brought into contact with the sample bound on the solid substrate. After a suitable period of incubation, for a period of time sufficient to allow formation of an antibody-antigen binary complex a second antibody, labeled with a reporter molecule capable of inducing a detectable signal, is then added and incubation is continued allowing sufficient time for the formation of a ternary complex of antigen-antibody-labeled antibody. For the single site immunoassay, the second antibody may be a general antibody (i.e., zenogeneic antibody to immunoglobulin, particularly anti-(IgM and IgG) linked to a reporter molecule) that is capable of binding an antibody that is specific for the tagged protein of interest.

Commercially available, conventional anti-tag mAbs are mostly, if not all, made from mouse. The mouse anti-tag mAbs are not readily usable for the studies on mouse tissues or in vivo applications in mouse, unless they are directly labeled with fluorochromes, enzymes, or other detectable means, which would make those materials rare and costly. Therefore, the new anti-OLLAS tag mAb OLLA-2 from rat IgG will provide an extra advantage over conventional mouse anti-tag mAbs, as the inventors have illustrated that mAb OLLA-2 can be used directly in mouse in vivo and detected in mouse tissues without special, direct labelings.

Selected embodiments will not be further discussed in the following example. The example is illustrative only, and is not intended to limit the instant disclosure in any way.

EXAMPLES

Materials and Methods

Production of Epitope Specific MAb hybridoma.

Animals and cell lines: Wistar Furth rats were purchased from Charles River Laboratories (Wilmington, Mass.). C57BL/6 and BALB/c mice were purchased from Taconic Farms (Hudson, N.Y.) and Charles River Labs, and used at 6-8 wks of age. All animals were maintained under specific pathogen-free conditions. Animal care and experiments were conducted according to institutional guidelines of the Rockefeller University and Memorial Sloan-Kettering Cancer Center.

Chinese hamster ovary (CHO) cells and 293T cells were cultured in DMEM with 7% FBS or 5% Ultra-Low IgG FBS supplemented with 2mM glutamine (Gibco BRL, Invitrogen, Carlsbad, Calif.), antibiotics (Invitrogen) and non-essential amino acids (Invitrogen).

MAb hybridoma production: Generation and screening of mAb hybridomas against FLAG/OFL tagged mLangerin ECD were described previously (Cheong et al., *J Immunol Methods*. 2007 324(1-2):4842 (2007)). In brief, Wistar Furth rats were immunized with the purified proteins of mLangerin ECD fused with OFL and human IgG1 Fc (GenBank accession no. DQ917567, SEQ ID NO: 25) and FLAG/OFL tagged mLangerin ECD (GenBank accession no. DQ917568, SEQ ID NO: 26), followed by the injection of mouse dendritic cells enriched from ear skin organ cultures (Cheong et al., 2007). Then, the cells from spleen were used for hybridoma fusion at the Monoclonal Antibody Core Facility of the Rockefeller University and Memorial Sloan Kettering Cancer Center. Culture supernatants from the hybridomas were screened on ELISA with FLAG/OFL tagged mLangerin ECD protein as previously described (Cheong et al., 2007).

Reagents: To purify mAbs L2, L5, L31 and NLDC145, the supernatants of individual hybridomas were cultured and the mAbs were purified with protein G (Pierce, Rockford, Ill.; GE Healthcare, Piscataway, N.J.) column, according to the manufacture's instructions. The following reagents were purchased; ANTI-FLAG® M2, DAPI (Sigma-Aldrich, St. Louis, Mo.), anti-beta actin (Abcam Inc., Cambridge, Mass.), anti-human CD8 (Santa Cruz Biotechnology, Inc., Santa Cruz, Calif.), pEGFP-N1, anti-GFP (Clontech, Mountain View, Calif.), anti-B220 (BD Biosciences, San Jose, Calif.), anti-V5 (Invitrogen), HRP-conjugated anti-mouse IgG and HRP- or PE-conjugated anti-rat IgG (Southern Biotech, Birmingham, Ala.), PE-conjugated anti-mouse IgG (Jackson ImmunoResearch Laboratories, Inc., West Grove, Pa.), Alexa350-, Alexa488- or Alexa647-conjugated anti-rat IgG and Alexa647-conjugated anti-mouse IgG (Molecular Probes, Invitrogen).

Vector constructions and expression of recombinant proteins: The construction, expression and purification of murinized heavy and light chains for anti-DEC205 mAb NLDC145 (mNLDC145) and isotype control mAb have been described (Hawiger et al., *J Exp Med*. 194(6):769-779 (2001)). The sequences of OLLAS peptide (SGFANELGPRLMGK/SEQ ID NO: 1; GenBank accession no. EF635496, SEQ ID NO: 27) or OLLAS-tagged ovalbumin (GenBank accession no. EF635488, SEQ ID NO: 28) were inserted at the carboxy-terminus in heavy chains of mNLDC145 or isotype control mAbs. 293T cells were transfected with the expression vectors for mNLDC145 or isotype control mAbs carrying OLLAS-tagged inserts. Then, the culture supernatants or mAbs purified by Protein G affinity column were used for further analyses. Soluble FLAG-mLangerin.ECD protein was purified from culture supernatants of the stable CHO/FLAG-mLangerin.ECD cells by ANTI-FLAG® M1 Affinity Gel (Sigma-Aldrich) following the manufacturer's instruction.

The generation of expression vectors for the open reading frames (ORFs) of full-length mLangerin and soluble fusion mLangerin ECD with FLAG/OFL was described previously (Cheong et al., 2007). The cDNAs for epitope tags or subdomains of individual genes were generated by PCR, sequenced, and ligated to make the ORFs for respective recombinant fusion proteins. Then, the ORFs were cloned into pCMV mammalian expression vector (Clontech) and stably transfected into CHO cells or transiently transfected to 293T cells. The expression vectors for the ORFs of following recombinant proteins were generated; FLAG-mLangerin. ECD (GenBank accession no. EF635489, SEQ ID NO: 29), FLAG-OFL/2-mLangerin.ECD (GenBank accession no. EF635490, SEQ ID NO: 30), FLAG-mSIGN-R1.ECD (GenBank accession no. EF635491, SEQ ID NO: 31), rat P11-FLAG.HA (GenBank accession no. EF635492, SEQ ID NO: 32), human CD8.ECD-OFL-mLangerin.ECD (GenBank accession no. EF635493, SEQ ID NO: 33), hCD8.ECD-OFL-mLangerin.ECD.deletion.#1 (GenBank accession no. EF635494, SEQ ID NO: 34), hCD8.ECD-OFL-mLangerin.ECD.deletion.#2 (GenBank accession no. EF635495, SEQ ID NO: 35), OT1-EGFP-OLLAS (GenBank accession no. EF635497, SEQ ID NO: 36), FLAG.OLLAS-EGFP (GenBank accession no. EF635498, SEQ ID NO: 37). V5-hIgG1Fc-OLLAS was generated from V5-hIgG1Fc-OFL-mLangerin.ECD (GenBank accession no. DQ917567, SEQ ID NO: 25; Cheong et al., 2007) by replacing OFL-mLangerin.ECD with OLLAS. OLLAS-EGFP and mSIGN-R1.Cytosol-OLLAS-EGFP were generated by inserting OLLAS or mSIGN-R1.Cytosol-OLLAS (GenBank accession no. EF635499, SEQ ID NO: 38) sequences into the multi-cloning site of pEGFP-N1 vector (Clontech).

Characterization of mAbs.

SDS-PAGE and Western blot analysis: 293T cells were transfected with the expression vectors for recombinant fusion proteins, harvested at day 2, lysed in RIPA buffer (150 mM NaCl, mM Tris-HCl, pH 8.0, 1% Nonident P-40, 0.5% sodium deoxycholate and 0.1% SDS) supplemented with protease inhibitor cocktails (Sigma-Aldrich), and stored at −20° C. Each lysed sample was mixed with an equal volume of 2×SDS PAGE sample buffer and boiled at 95° C. for 5 min. Then the samples were separated in 12 or 15% SDS-PAGE and transferred onto PVDF membranes, followed by incubation with antibodies. Antibody-reactive bands on the blots were visualized by incubation with peroxidase-labeled secondary Ab followed by treatment with ECL Plus™ reagents (GE Healthcare). The isotypes of mAb heavy and light chains were determined by the Western blot analysis using mAb supernatant as primary Ab and rat isotype specific HRP-conjugated Abs (Southern Biotech) as secondary Ab.

Immunofluorescence: Stably transfected CHO cells and lymph nodes sections were examined for immunofluorescence as described previously. (Kang et al, Int Immunol. (2):177-86 (2003); Kang et al, Proc Natl Acad Sci USA. 101(1):215-220(2004)). Cells cultured on slides were washed with PBS, fixed in acetone for 5 min, and subsequently washed and blocked with PBS with 3% BSA for 1 hr. Then, after incubation with primary Abs for 1 hr at room temperature, cells were washed and incubated with fluorochrome-labeled secondary Abs. For tissue staining, peripheral lymph nodes from C57BL/6 mice were collected and embedded in Tissue-Tek OCT® (optimal cutting temperature) compounds (Sakura Finetek USA, Torrance, Calif.) before freezing at −80° C. Frozen tissues were sectioned 10 μm in thickness on a microtome and fixed in cold acetone for 15 min. Sections were incubated with primary Abs at room temperature in a humidified chamber for 1 hr, washed and then incubated with fluorochrome-labeled secondary Abs. Sections were mounted in Aqua-Poly Mount (Polysciences, Warrington, Pa.) and were stored at 4° C. until microscopic examination. The images were acquired with a deconvolution microscopy (Olympus, Melville, N.Y.) or with a Zeiss LSM 510 system (Carl Zeiss MicroImaging, Thornwood, N.Y.) at the Rockefeller University Bio-Imaging Resource Center.

FACS analysis: After detaching with 1 mM EDTA in PBS for 10 min, CHO/mDEC205 cells were incubated with primary Abs for 15 min at 4° C. Cells were washed, detected by Alexa 647 conjugated secondary Abs for 15 min at 4° C., and analyzed with FACSCalibur flow cytometer (BD Biosciences) at the Rockefeller University Flow Cytometry Resource Center.

Sequence analysis: The sequences of OFL and OLLAS were analyzed by PSIPRED (Bryson et al., *Nucleic Acids Res.* 33(Web Server issue), W36. (2005); McGuffin et al., *Bioinformatics* 16(4):404-405 (2000)) using the PSIPRED Protein Structure Prediction Server, and the NCBI BLAST database were searched for the sequence similarities.

Example 1

MAb L5 Recognizes the FLAG Epitope and L2 Recognizes an OFL Dependent Tag

To identify the epitopes of newly generated rat IgG mAbs L2 and L5, the inventors first made different forms of recombinant mLangerin proteins with/without *E. coli* OmpF derived flexible linker (OFL) sequences (FIG. 1A), which consisted of 17 amino acid residues, NATPITNKFTNTSG-FAN (SEQ ID NO: 18). FLAG epitope tags with full or half-deleted OFL or without OFL were fused to the N-terminus of mLangerin extracellular domain (ECD) for which a specific L31 mAb was recently obtained and described (Cheong et al., 2007). These constructs were cloned into CMV mammalian expression vectors and transfected to 293T cells. The cell lysates were subjected to Western blot analyses (FIG. 1B), using mAbs L2 and L5 in comparison with L31 (anti-mLangerin; Cheong et al., 2007) and the commercial mAb M2 (ANTI-FLAG® from Sigma Aldrich). The results indicated that, while anti-mLangerin mAb L31 recognized all the recombinant proteins containing mLangerin ECD, mAb L2 only detected the two recombinant proteins containing OFL sequences (FIG. 1B, lanes 3 & 4). Since constructs containing mLangerin ORF (FIG. 1B, lane 1) or FLAG only (FIG. 1B, lane 5) were not detected by mAb L2, the epitope of mAb L2 is different from the epitopes identified by anti-mLangerin L31 and anti-FLAG M2. Interestingly, mAb L2 could detect the construct containing half-deleted OFL sequence (FIG. 1B, lane 4) where two N-glycosylation sites in OFL were removed (FIG. 3C) and where two N-terminal amino acids were absent from the OLLAS epitope of SEQ ID NO: 1 (See FIG. 1B, lane 4).

Another newly generated mAb L5 was specifically reactive to all the recombinant proteins containing a FLAG sequence, but not mouse Langerin itself, similarly to anti-FLAG mAb M2 (FIG. 1B). Thus, mAb L5 is a new rat IgG mAb against the FLAG epitope. The inventors also have used mAb L5 efficiently in the immunoprecipitation and immunofluorescent detection of FLAG tagged recombinant proteins (data not shown).

Example 2

Comparison of Anti-FLAG Binding Sensitivity Between Rat IgG mAb L5 and a Commercially Available Mouse IgG mAb M2

Figure 2B:
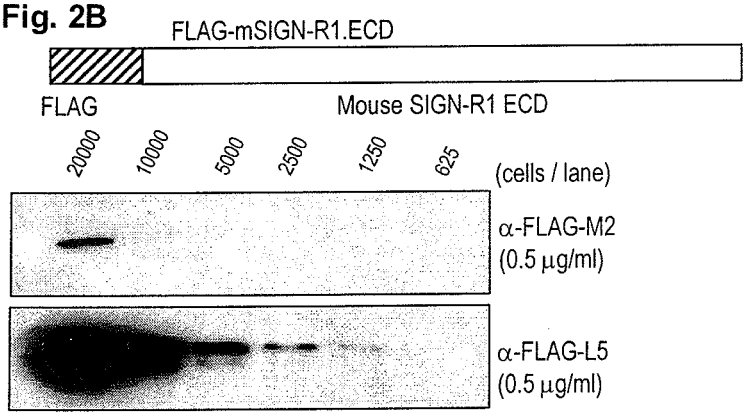
Figure 2C:
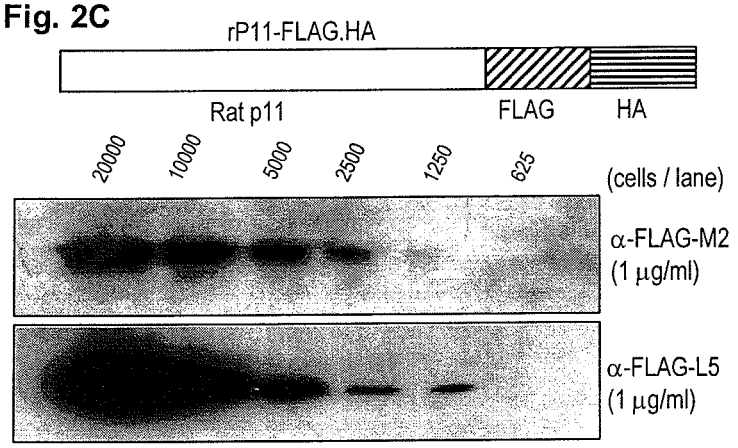

To compare the binding sensitivity to the FLAG epitope between mouse IgG mAb M2 and the new rat IgG mAb L5, the inventors performed Western blot analyses with different FLAG tagged proteins. First, the purified protein of N-terminal FLAG tagged mLangerin ECD was loaded in serial, two-fold dilutions (FIG. 2A). The serially diluted samples were blotted in 1 μg/ml of anti-FLAG mouse IgG mAb M2 or rat IgG mAb L5, followed by detection with secondary anti-mouse IgG or anti-rat IgG antibodies respectively. The results with the two anti-FLAG mAbs indicated that mAb L5 could detect the FLAG tagged protein at 4 fold lower amounts than M2 mAb (FIG. 2A). The inventors also performed Western blot analyses with FLAG-mSIGN-R1.ECD, another N-terminal FLAG tagged recombinant protein. The cell lysate of 293T cells transfected with FLAG-mSIGN-R1.ECD construct was analyzed in serial, two-fold dilution with mAbs M2 and L5 as above. Similar to the results from purified, N-terminal FLAG tagged protein, mAb L5 could detect anti-FLAG signals in the cell lysates with 8 fold fewer cells (FIG. 2B). To test whether the location of FLAG epitope tag could affect the binding sensitivity, a rP11-FLAG.HA construct was made, in which the FLAG epitope was inserted at the C-terminus of rat p11 ORF (FIG. 2C), and transfected into 293T cells. Again in this C-terminal FLAG tagged recombinant protein, mAb L5 could detect FLAG in cell lysates from as little as 1250 cells, whereas the detection of mAb M2 required cell lysates from 2500 cells (FIG. 2C). Therefore, mAb L5 detects both N-terminal and C-terminal FLAG tagged proteins 2-8 times better than the conventional anti-FLAG mAb M2.

Example 3

Mapping of the Epitope Detected by mAb L2, Renamed OLLA-2

Figure 3A:
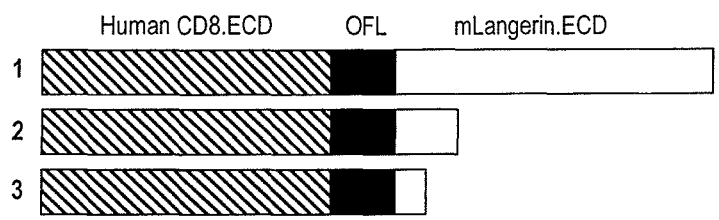
FIGS. 3A, 3B, and 3C present results of mapping of the epitope tag OLLAS. The epitope of mAb L2 (renamed OLLA-2) is a fusion sequence between OFL and mLangerin ECD. (3A) Schematic view of serial deletions in hCD8.ECD-OFL-mLangerin.ECD fusion proteins. (3B) The series of C-terminal deletion constructs in FIG. 3A were transfected into 293T cells, followed by Western blot analyses with anti-hCD8 (left panel) and mAb OLLA-2 (right panel). (3C) The 14 amino acid sequence, named OLLAS (*E. coli* OmpF Linker mouse Langerin fusion Sequence, SEQ ID NO: 1), residues from both OFL (SEQ ID NO: 18) and mLangerin ECD (SEQ ID NO: 19) was identified as the epitope recognized by mAb OLLA-2. The 3 amino acid residues (ELG) in the middle of OLLAS epitope correspond to the junction sequence from the ligation between DNAs for OFL and mLangerin ECD. The 2 Asn (N) residues circled are potential sites for N-glycosylation in OFL. Also shown is the sequence of the fusion protein of OFL and mLangerin ECD (SEQ ID NO: 20).
Figure 3B:
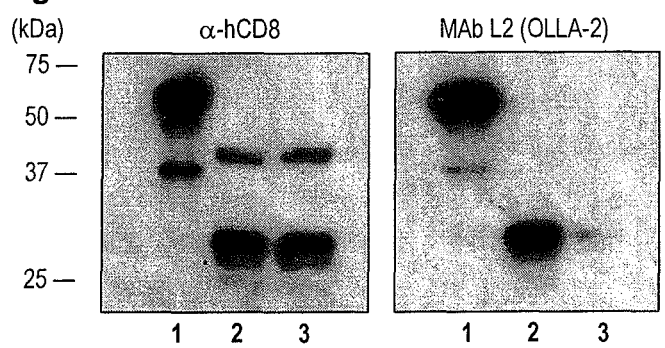

As shown in FIG. 1, mAb L2 recognized an undefined epitope in OFL-mLangerin ECD, indicating the C-terminal half of OFL was required to be detected by mAb L2. To map the epitope recognized by OLLA-2, the inventors designed serial deleted constructs. First, mLangerin ECD was fused with human CD8 ECD with OFL, and serial deletions were made from the C-terminus (FIG. 3A). 293T cells were transfected with each construct, lysed, followed by the Western blotting with anti-hCD8 (FIG. 3B, left panel) and mAb L2 (FIG. 3B, right panel). The results showed that the epitope of mAb L2 included the N-terminal region of the mLangerin ECD (FIG. 3B, right panel, lanes 2 & 3). Subsequently, the 14 amino acid peptide epitope recognized by mAb L2 as SGFANELGPRLMGK (SEQ ID NO: 1, FIG. 3C) was defined and named the tag, OLLAS (*E. coli* OmpF Linker and mouse Langerin fusion Sequence). The inventors also renamed mAb L2 as mAb OLLA-2. Notably, the construct comprising the fragment of OLLAS lacking three amino acids at C-terminus of SEQ ID NO: 1 did not bind mAb OLLA-2 as well as the construct having these three amino acids (compare lns 2 and 3 in the right panel of FIG. 3B).

Example 4

Figure 4:
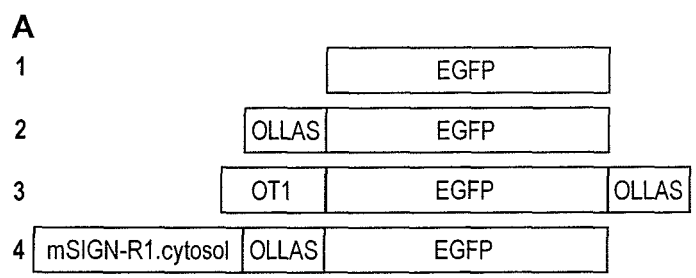
FIGS. 4A, 4B, and 4C present the results of immunodetection of OLLAS tagged EGFP proteins. (4A) Schematic view of 4 recombinant EGFP proteins without a tag (1) or with OLLAS epitope tag attached to the N-terminus (2), C-terminus (3), or internal site (4). The OT1 peptide, a ligand of mouse MHC I from ovalbumin, were also present in the N-terminus of EGFP protein 3. The 53 amino acid full-length cytosolic domain from mouse SIGN-R1 was present at the N-terminus of EGFP protein 4. (4B) Expression vectors for the 4 different recombinant EGFP proteins were transfected into 293T cells. Cell lysates (left) were immunoprecipitated (IP) with mAb OLLA-2 (right). Then, all samples were separated in SDS-PAGE gels followed by blotting with anti-GFP (upper panels) and mAb OLLA-2 (lower panels). (4C) Expression vectors for EGFP (1; upper panels) and EGFP with OLLAS tag at the N-terminus (2; lower panels) were transfected into CHO cells. CHO cells were visualized with the signals for EGFP and immunofluorescence staining for OLLA-2. Insets in left panels are shown at 1000 fold magnification in the right.
Figure 4:
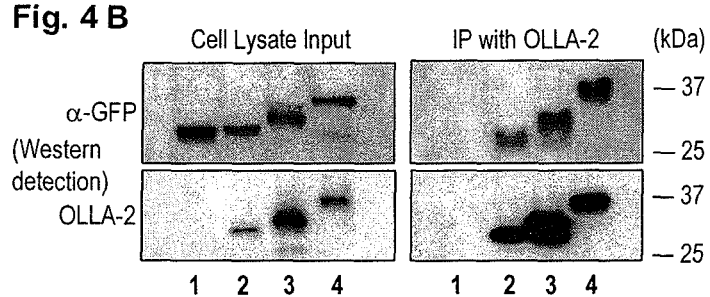
Figure 4:
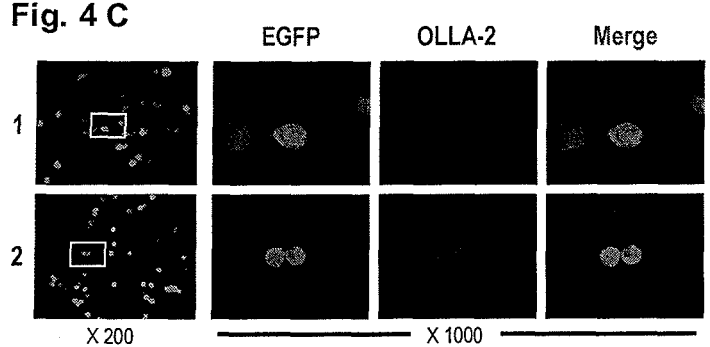

The Use of OLLAS Epitope as a Tag for Immunodetection and Immunoprecipitation of Recombinant EGFP Proteins To confirm the use of the new OLLAS epitope as a tag to detect fusion proteins, the OLLAS sequence (SGFANELG-PRLMGK, SEQ ID NO: 1) to the N-terminus, the C-terminus, and internal sites of recombinant EGFP proteins was fused (FIG. 4A). The expression vectors for these recombinant EGFP proteins were transfected into 293T cells. The cell lysates were subjected to SDS-PAGE followed by Western blot detection with anti-GFP and mAb OLLA-2 (FIG. 4B, left panels). Then, these cell lysates were subjected to immunoprecipitation with mAb OLLA-2 followed by the Western blot detection of the immunoprecipitates with anti-GFP and mAb OLLA-2 (FIG. 4B, right panels). Detection by anti-GFP or mAb OLLA-2 was clearly visible by Western blot analyses of the cell lysates regardless of the location of the OLLAS epitope (FIG. 4B, left panels). Detection of the immunoprecipitates by anti-GFP indicated that successful immunoprecipitation was also achieved with OLLAS epitope tagged proteins by mAb OLLA-2 (FIG. 4B, right panels). In addition, the expression vectors for EGFP alone and OLLAS tagged EGFP were transfected into CHO cells to test immunofluorescent staining of cells with mAb OLLA-2. Only the OLLAS epitope tagged EGFP was co-stained with mAb OLLA-2 (FIG. 4C, lower panels), indicating that the OLLAS epitope is suitable for the fluorescent immunocytochemistry. These data demonstrate that OLLAS is a superior tag for immunodetection of OLLAS-tagged proteins.

Example 5

Figure 5A:
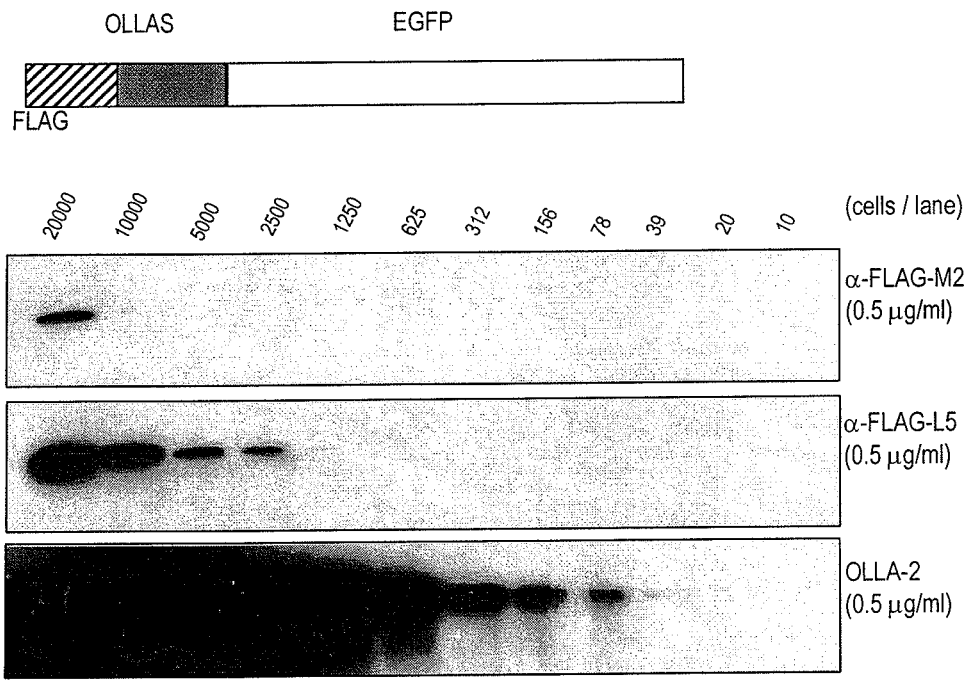
FIGS. 5A and 5B present the results of comparison binding sensitivity of mAb OLLA-2 and other anti-epitope tag mAbs. (5A) 293T cells were transfected with pCMV-FLAG.OLLAS-EGFP (structure shown in upper panel), lysed, diluted as indicated, and separated in SDS-PAGE gels followed by blotting with 0.5 μg/ml of anti-FLAG mAb M2 (second panel), the new anti-FLAG mAb L5 (third panel), and mAb OLLA-2 (lower panel). (5B) 293T cells were transfected with pCMV-V5-hIgG1Fc-OLLAS (structure shown in upper panel), lysed, diluted as indicated, and separated in SDS-PAGE gels followed by blotting with 1 μg/ml of anti-V5 mAb (Invitrogen; middle panel) and mAb OLLA-2 (lower panel).

Comparison of Binding Sensitivity of mAb OLLA-2 and Other Anti-Epitope Tag mAbs by Western Blot Analyses To compare the binding sensitivity of anti-OLLAS tag mAb OLLA-2 with anti-FLAG tag mAbs M2 and L5, EGFP protein was fused with FLAG and OLLAS tag in tandem at the N-terminus (FIG. 5A). 293T cells were transfected with this FLAG.OLLAS-EGFP expression vector, lysed, and analyzed in serial, two-fold dilutions by Western blotting with 0.5 μg/ml of anti-FLAG mAbs M2 and L5 as well as mAb OLLA-2 (FIG. 5A). The result shows that mAb OLLA-2 binds to its OLLAS epitope with at least 100-fold more sensitivity than anti-FLAG mAb M2 and with at least 30-fold more sensitivity than anti-FLAG mAb L5.

Figure 5B:
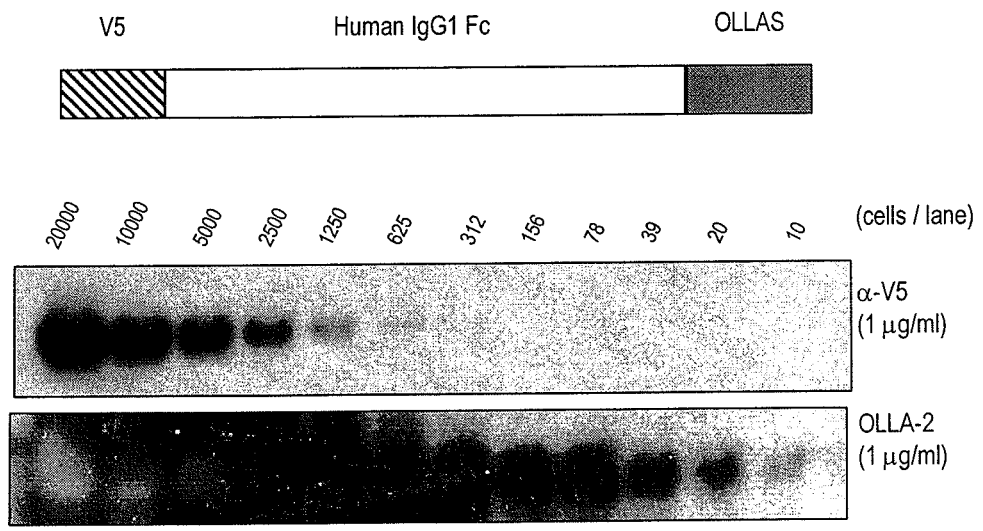

Next, to compare the binding sensitivity of mAb OLLA-2 with anti-V5 mAb (Invitrogen catalog number R960), human IgG1 Fc protein was fused with V5 epitope at the N-terminus and with OLLAS epitope at the C-terminus (FIG. 5B). 293T cells were transfected with this V5-hIgG1Fc-OLLAS expression vector, lysed, and analyzed in serial, two-fold dilutions for the Western blotting with 1 μg/ml of anti-V5 mAb and mAb OLLA-2 (FIG. 5B). The results showed that mAb OLLA-2 bound to its OLLAS epitope with at least 100-fold more sensitivity than anti-V5 mAb. These findings indicate that the OLLA-2 mAb possesses very strong affinity for the OLLAS epitope, i.e. SGFANELGPRLMGK (SEQ ID NO: 1), and reacts specifically with recombinant proteins containing this epitope.

Example 6

OLLAS Epitope is a Suitable Tag on Engineered mAb for Immunodetection

Figure 6A:
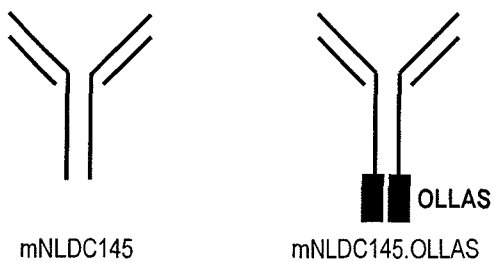
FIGS. 6A and 6B illustrate production of murinized anti-mouse DEC205 mAb mNLDC145 expressing the OLLAS tag. (6A) Schematic view of the anti-mDEC205 mAb mNLDC145 engineered so that all rat constant domains are replaced with mouse IgG1 sequences (left) and OLLAS tagged mAb mNLDC145.OLLAS (right). (6B) Expression vectors for mNLDC145 and mNLDC145.OLLAS were transfected into 293 cells. In 2 days, the culture supernatants from transiently transfected cells were collected and separated in SDS-PAGE gels followed by blotting with anti-mouse IgG (upper panel) and mAb OLLA-2 (lower panel).
Figure 6B:
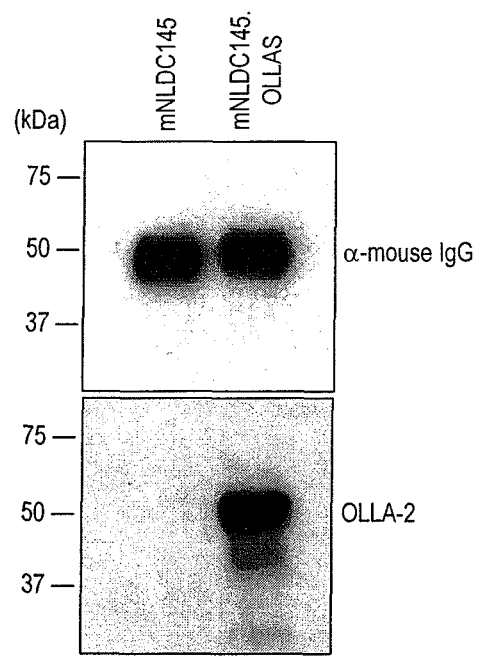

To test whether the OLLAS epitope was suitable as a tag for engineered mAbs, the sequence was fused to the C-terminus of the heavy chain of murinized NLDC145 (mNLDC145; FIG. 6A), a cloned and engineered anti-mouse DEC205 mAb (Hawiger et al., 2001). The culture supernatants from 293T cells, which had been transiently transfected with mNLDC145 or mNLDC145.OLLAS expression vectors, were collected and separated in SDS-PAGE gels followed by Western blotting with anti-mouse IgG (FIG. 6B, upper panel)

and mAb OLLA-2 (FIG. 6B, lower panel). The OLLA-2 mAb was specific for the engineered mNLDC145.OLLAS mAb.

To confirm the usage of OLLAS epitope as a tag for engineered mAbs, the culture supernatants from 293T cells transfected with mNLDC145 or mNLDC145.OLLAS expression vectors were used for FACS analysis. Stable CHO cells expressing mDEC205 (CHO/mDEC205 cells) were incubated with each supernatant and stained with mAb OLLA-2 followed PE-conjugated anti-rat IgG prior to flow cytometry (FIG. 7A). The result showed that only mNLDC145.OLLAS with mAb OLLA-2 was able to stain the CHO/mDEC205 cells. For fluorescent immunocytochemistry, CHO/mDEC205 cells were incubated with the culture supernatants containing mNLDC145 or mNLDC145.OLLAS (FIG. 7B). Then, cells were stained with anti-mouse IgG and mAb OLLA-2 with anti-rat IgG. The result showed that the OLLA-2 signal co-localized with anti-mouse IgG, i.e. mNLDC145, signal only when mNLDC145.OLLAS supernatant was used (FIG. 7B, right panel).

For fluorescent immunohistochemistry, mouse lymph nodes were incubated with rat IgG control, rat IgG mAb NLDC145, or engineered mNLDC145.OLLAS respectively. Subsequently, all lymph nodes were further stained with mAb OLLA-2 and anti-rat IgG labeled with Alexa488 and anti-B220. These results showed that mAb OLLA-2 was specific and sensitive to the OLLAS epitope and that there was no non-specific, background signals in the tissue staining of lymph nodes. These findings confirm that the OLLAS epitope and mAb OLLA-2 is broadly useful in various immunodetection methods, including FACS analysis and fluorescent immunostaining.

Example 7

Improved Immunodetection with OLLAS Epitope Tag

As shown in FIG. 7C, murinized mAb mNLDC145.OLLAS was able to detect mDEC205 in sections of lymph node tissues (FIG. 7C, lower panels), whereas rat IgG mAb NLDC145 was not sensitive enough (FIG. 7C, middle panels). This might be explained because the detection of mNLDC145.OLLAS required the secondary mAb OLLA-2 followed by the fluorescent labeled tertiary anti-rat IgG Ab, while the detection of NLDC145 required only the fluorescent labeled anti-rat IgG Ab.

In order to compare directly the use of mNLDC145.OLLAS and mAb OLLA-2, two engineered mAbs with the OLLAS epitope tag were generated (FIG. 8A). Expression vectors for murinized isotype control mAb fused with OLLAS epitope and ovalbumin (mIsotype.OLLAS.OVA) and mAb mNLDC145 fused with OLLAS epitope and ovalbumin (mNLDC145.OLLAS.OVA) were transfected into 293T cells. Then, mIsotype.OLLAS.OVA and mNLDC145.OLLAS.OVA mAbs were purified from culture supernatants. MAb OLLA-2 were also purified and then labeled with Alexa647 fluorochrome. As shown in FIG. 8B, under the same conditions, CHO/mDEC205 cells incubated with mNLDC145.OLLAS.OVA were better detected by Alexa647 labeled OLLA-2 than Alexa647 labeled anti-mouse IgG.

Then, the inventors examined the lymph node tissues stained with either engineered mAb mNLDC145.OLLAS.OVA or rat mAb NLDC145 followed by visualization with Alexa647 labeled OLLA-2 and Alexa647 labeled anti-rat IgG, respectively (FIG. 8C). Unlike the previous result of lymph modes staining by mAb NLDC145 with Alexa488 labeled anti-rat IgG (FIG. 7C, middle panels), mAb NLDC145 with Alexa647 labeled anti-rat IgG was able to detect mDEC205 in sections of lymph node tissues (FIG. 8C, left panel) as efficiently as mAb mNLDC145.OLLAS.OVA with Alexa647 labeled OLLA-2 (FIG. 8C, right panel). These results demonstrate that OLLAS epitope is a useful tag for engineered mAbs, which then can be used better than or as efficiently as original mAbs in various applications of immunodetection. It was also found that the use of OLLAS peptide as an inter-molecular linker between two recombinant proteins, such as in mNLDC145.OLLAS.OVA and mIsotype.OLLAS.OVA, improved the expression of recombinant fusion proteins (data not shown) without losing its role as a highly effective epitope tag in various immunodetections.

Example 8

Analysis of Secondary Structures of OFL and OLLAs Sequences

Figure 9:
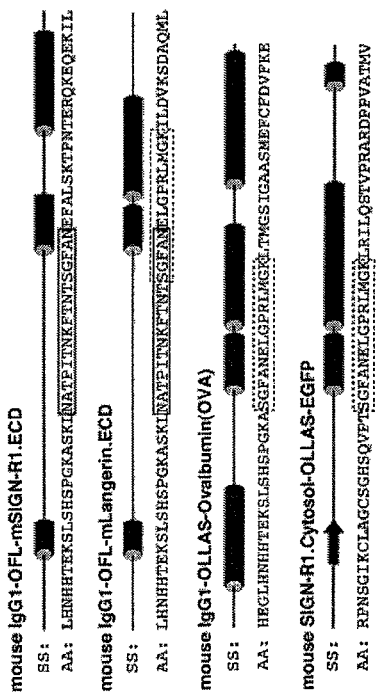
FIG. 9 presents results of a secondary structure (SS) analysis of the amino acid (AA) sequences of OFL (solid box) and OLLAS (dashed box) linkers located in four fusion proteins (from top to bottom, SEQ ID NOs: 21-24, respectively). Straight lines in SS represent random coil conformations, cylinders helical conformations, and an arrow extended (sheet) conformation. Note that both OFL and OLLAS sequences coexist in mouse IgG1-OFL-mLangerin.ECD (SEQ ID NO: 22).

A secondary structure prediction program called PSIPRED (Bryson et al., 2005; McGuffin et al., 2000) was utilized to characterize possible conformations of the OFL and OLLAS sequences used in-between the fused proteins that were generated successfully in previous (Galustian et al., *Int Immunol*. 16(6):853-866 (2004)) and current studies. As shown in FIG. 9, 20 amino acids before and after the OFL and OLLAS linkers were included into the query sequences to increase the accuracy of the predicted secondary structures. The OFL linker mostly adopts a random coil conformation, while the OLLAS linker shows a strong propensity to form an α-helical conformation.

In a non limiting way, the instant invention may be summarized as follows.

Monoclonal antibodies against epitope tags are an efficient, convenient and rapid method for detecting recombinant protein expression (Jarvik and Telmer, 1998). If there is no antibody against the protein of interest, adding an epitope tag to this protein allows for protein detection with an antibody against the epitope sequence. For example, affinity tags such as a FLAG-tag appended to recombinant proteins have traditionally been used as a way of purifying proteins using standard conditions rather than developing individual biochemical purifications based on each protein's physical characteristics (Hopp et al., 1988).

Previously, rats were immunized to produce anti-mLangerin/CD207 antibody using two different forms of fusion proteins for mLangerin ECD expressed and purified from culture supernatants of stably transfected CHO cells (Cheong et al., 2007). As fusion partners of mLangerin ECD, FLAG epitope and flexible linker sequences from *E. coli* OmpF protein (OFL) were used. FLAG epitope was chosen for column purification and OFL was chosen to facilitate the folding of fusion proteins and to increase secretion from the cells. The OFL sequence as a linker was initially employed because the OFL sequence was viewed as highly flexible based on the molecular dynamics simulation of OmpF from *E. coli* (Im and Roux, *J Mol Biol*. 319(5):1177-1197 (2002)). Although the OFL sequence forms a beta-hairpin loop in OmpF, the secondary prediction by PSIPRED (Bryson et al., 2005; McGuffin et al., 2000) indicates that the OFL exists as a flexible coil in-between the fused proteins. This prediction is corroborated by the successful expressions of fusion proteins for C-type lectins, which were functional in sugar binding activities (Galustian et al., 2004) as well as immunogenic in mAb productions (Kang et al., 2004; Cheong et al., 2007).

In the process, it was found that new mAbs L5 and OLLA-2 were specific to the FLAG/OFL tagged mLangerin ECD protein, not to mLangerin ECD. Applicants demonstrate that L5 is a new anti-FLAG mAb (FIG. 1) and OLLA-2 is a highly reactive mAb against a new epitope tag (FIGS. 1 and 3). The new anti-FLAG L5 mAb shows high sensitivity for the FLAG epitope and specificity for both N-terminally and C-terminally tagged FLAG epitope. In Western blot analyses, L5 can detect as little as 25 ng of N-terminally FLAG tagged purified protein (FIG. 2A) and lysates from 2,500 cells transfected with N-terminally FLAG tagged recombinant protein construct (FIG. 2B). Conventional anti-FLAG M2 can detect 100 ng of N-terminally FLAG tagged purified protein (FIG. 2A) and lysates from 20,000 cells transfected with N-terminally FLAG tagged recombinant protein construct (FIG. 2B). Besides highly enhanced reactivity against the FLAG epitope, the new anti-FLAG L5 is a rat IgG mAb and provides an additional option in immunostaining since all other conventional anti-FLAG antibodies are mouse monoclonals or rabbit polyclonals.

MAb L2 or OLLA-2 is a novel rat IgG mAb against the newly identified epitope (SGFANELGPRLMGK, SEQ ID NO: 1) named OLLAS, with many advantages in recombinant protein engineering and immunodetection. First, this novel pair of tag and anti-tag mAb has a remarkable sensitivity and thus enhances the performance of a variety of immunodetection methods, including Western blot, immunocytochemistry, immunohistochemistry, flow cytometry, and immunoprecipitation. Especially, mAb OLLA-2 can detect the OLLAS epitope tagged proteins by Western blotting with more than 100 fold higher sensitivity than anti-FLAG M2 and anti-V5 mAbs. Second, the new OLLAS epitope can be fused to the C-terminal, the N-terminal, and the internal (or linker) sites of recombinant and fusion proteins including the engineered mAbs. The OLLAS epitope does not interfere with the biological activities of the recombinant proteins where it was inserted, such as fluorescence of EGFP and binding of antibodies, and can improve the expression of recombinant proteins as an inter-molecular linker between two recombinant proteins, as shown in the engineering of anti-mDEC205 mAb fused with ovalbumin. Third, mAb OLLA-2, as a rat IgG, can be used for the immunostaining of mouse and human samples without direct labelling of fluorochrome or enzyme. Because anti-tag mAbs and Abs are mostly made from mouse and rabbit, the anti-OLLAS tag mAb OLLA-2 from rat IgG will provide an extra advantage in immunodetection.

Figure 3C:
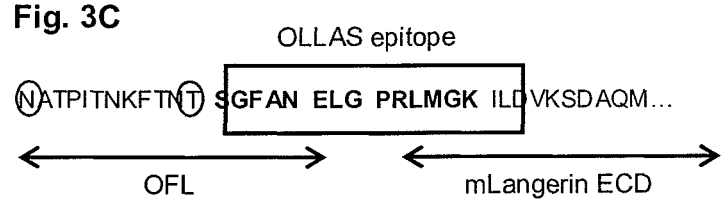

As indicated in FIG. 3C, the OFL sequence contains two N-glycosylation sites. It is possible that the N-glycosylation in OFL region could interfere with the structural integrity of the fusion proteins and/or the antibody responses against the fusion proteins where the OFL linker was used. However, the newly identified OLLAS epitope sequence does not have any N-glycosylation site. Unlike OFL, when the OLLAS are used as a linker in the fused proteins, it is predicted to adapt an alpha-helical conformation by PSIPRED (FIG. 9). It has been suggested that, in linker engineering, the helical linkers like OLLAS are better than flexible linkers like OFL to maximize the desired function of engineered fusion proteins (Arai et al., *Protein Eng.* 14(8): 529-532 (2001)). As demonstrated in FIG. 8, the OLLAS sequence appears to function properly as a linker in the engineered mAbs fused with antigens. In addition, the OLLAS sequence is a superior protein-tagging epitope to other currently existing tag epitopes. It should be stressed that the OLLAS, generated by fusion between the sequences from *E. coli* and mouse, is a synthetic sequence different from any of the known protein sequences in nature, indicated by the NCBI BLAST search. The uniqueness of its sequence may make the OLLAS tag more useful for many different applications in immunodetection, especially in vivo applications in diverse organisms.

Thus, the present invention provides that mAb L5 is a new anti-FLAG with higher sensitivity, and that the novel OLLAS epitope and mAb OLLA-2 are superior tag and anti-tag mAb in terms of highly sensitive detection, broader range of applications, sequence uniqueness, and potential use as a linker. These new epitope tag and anti-tag mAbs will improve the current immunodetection methods for recombinant proteins.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. An isolated antibody or an antigen-binding portion thereof which selectively binds to a polypeptide comprising the sequence of SEQ ID NO: 1 or a fragment thereof selected from the group consisting of SEQ ID NO: 4-SEQ ID NO: 17.

2. The antibody of claim 1, wherein the antibody is a rat IgG monoclonal antibody (mAb).

3. A kit comprising:
  a) a first antibody of claim 1 and
  b) a detection reagent suitable for detecting the first antibody; and
  c) a set of instructions.

4. The kit of claim 3, wherein the first antibody selectively binds to a polypeptide comprising the sequence of SEQ ID NO: 1.

5. The kit of claim 3 wherein the detection reagent comprises a secondary antibody.

6. The kit of claim 5, wherein the secondary antibody selectively binds to the first antibody.

7. The kit of claim 5, wherein the secondary antibody is labeled with a reporter molecule.

8. The kit of claim 7, wherein the reporter molecule is one selected from the group consisting of an enzyme, a fluorescent compound, a radioisotope, a chemiluminescent, and a bioluminescent molecule.

9. The kit of claim 8, wherein the enzyme is one selected from the group consisting of horseradish peroxidase, glucose oxidase, beta-galactosidase and alkaline phosphatase.

10. The kit of claim 8, wherein the fluorescent compound is fluorescein or rhodamine.

11. The kit of claim 3 further comprising a reporter molecule.

12. The kit of claim 3, wherein the first antibody is bound to a solid support.

13. The kit of claim 3, further comprising one or more selected from the group consisting of a cloning vector, a forward primer, a reverse primer, a ligase, a restriction endonuclease, competent cells, and a control.

14. The kit of claim 13, wherein the control is a vector comprising a DNA sequence that encodes an OLLAS-tagged protein.

15. The kit of claim 14, wherein the kit further comprises a second antibody that selectively binds to the OLLAS-tagged protein.

16. The kit of claim 15, wherein the second antibody is labeled with a reporter molecule.

17. The kit of claim 16, wherein the reporter molecule is one selected from the group consisting of an enzyme, a fluorescent compound, a radioisotope, a chemiluminescent, and a bioluminescent molecule.

18. The antibody of claim 1, wherein the antibody is a monoclonal antibody.

19. The antibody of claim 1, wherein the antibody is a chimeric antibody.

20. The antibody of claim 1, wherein the antibody is a humanized antibody.

* * * * *

SEQUENCE LISTING

```
<160> NUMBER OF SEQ ID NOS: 38

<210> SEQ ID NO 1
<211> LENGTH: 14
<212> TYPE: PRT
<213> ORGANISM: Artificial Sequence
<220> FEATURE:
<223> OTHER INFORMATION: immunodetection tag

<400> SEQUENCE: 1

Ser Gly Phe Ala Asn Glu Leu Gly Pro Arg Leu Met Gly Lys
1               5                   10

<210> SEQ ID NO 2
<211> LENGTH: 42
<212> TYPE: DNA
<213> ORGANISM: Artificial Sequence
<220> FEATURE:
```

```
<223> OTHER INFORMATION: nucleic acid sequence encoding an
      mmunodetection tag

<400> SEQUENCE: 2
agtggctttg cgaatgaatt gggacctagg ttgatgggca ag                        42

<210> SEQ ID NO 3
<211> LENGTH: 8
<212> TYPE: PRT
<213> ORGANISM: Artificial Sequence
<220> FEATURE:
<223> OTHER INFORMATION: immunodetection tag

<400> SEQUENCE: 3

Asp Tyr Lys Asp Asp Asp Asp Lys
1               5

<210> SEQ ID NO 4
<211> LENGTH: 8
<212> TYPE: PRT
<213> ORGANISM: Artificial Sequence
<220> FEATURE:
<223> OTHER INFORMATION: immunodetection tag

<400> SEQUENCE: 4

Asn Glu Leu Gly Pro Arg Leu Met
1               5

<210> SEQ ID NO 5
<211> LENGTH: 9
<212> TYPE: PRT
<213> ORGANISM: Artificial Sequence
<220> FEATURE:
<223> OTHER INFORMATION: immunodetection tag

<400> SEQUENCE: 5

Ala Asn Glu Leu Gly Pro Arg Leu Met
1               5

<210> SEQ ID NO 6
<211> LENGTH: 10
<212> TYPE: PRT
<213> ORGANISM: Artificial Sequence
<220> FEATURE:
<223> OTHER INFORMATION: immunodetection tag

<400> SEQUENCE: 6

Phe Ala Asn Glu Leu Gly Pro Arg Leu Met
1               5                   10

<210> SEQ ID NO 7
<211> LENGTH: 11
<212> TYPE: PRT
<213> ORGANISM: Artificial Sequence
<220> FEATURE:
<223> OTHER INFORMATION: immunodetection tag

<400> SEQUENCE: 7

Gly Phe Ala Asn Glu Leu Gly Pro Arg Leu Met
1               5                   10

<210> SEQ ID NO 8
<211> LENGTH: 12
<212> TYPE: PRT
<213> ORGANISM: Artificial Sequence
<220> FEATURE:
<223> OTHER INFORMATION: immunodetection tag
```

```
<400> SEQUENCE: 8

Ser Gly Phe Ala Asn Glu Leu Gly Pro Arg Leu Met
1               5                   10

<210> SEQ ID NO 9
<211> LENGTH: 9
<212> TYPE: PRT
<213> ORGANISM: Artificial Sequence
<220> FEATURE:
<223> OTHER INFORMATION: immunodetection tag

<400> SEQUENCE: 9

Asn Glu Leu Gly Pro Arg Leu Met Gly
1               5

<210> SEQ ID NO 10
<211> LENGTH: 10
<212> TYPE: PRT
<213> ORGANISM: Artificial Sequence
<220> FEATURE:
<223> OTHER INFORMATION: immunodetection tag

<400> SEQUENCE: 10

Ala Asn Glu Leu Gly Pro Arg Leu Met Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: immunodetection tag

<400> SEQUENCE: 11

Phe Ala Asn Glu Leu Gly Pro Arg Leu Met Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: immunodetection tag

<400> SEQUENCE: 12

Gly Phe Ala Asn Glu Leu Gly Pro Arg Leu Met Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: immunodetection tag

<400> SEQUENCE: 13

Ser Gly Phe Ala Asn Glu Leu Gly Pro Arg Leu Met Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: immunodetection tag
```

<400> SEQUENCE: 14

Asn Glu Leu Gly Pro Arg Leu Met Gly Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: immunodetection tag

<400> SEQUENCE: 15

Ala Asn Glu Leu Gly Pro Arg Leu Met Gly Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: immunodetection tag

<400> SEQUENCE: 16

Phe Ala Asn Glu Leu Gly Pro Arg Leu Met Gly Lys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: immunodetection tag

<400> SEQUENCE: 17

Gly Phe Ala Asn Glu Leu Gly Pro Arg Leu Met Gly Lys
1               5                   10

<210> SEQ ID NO 18
<211> LENGTH: 17
<212> TYPE: PRT
<213> ORGANISM: Artificial Sequence
<220> FEATURE:
<223> OTHER INFORMATION: OmpF derived flexible linker (OFL) sequences

<400> SEQUENCE: 18

Asn Ala Thr Pro Ile Thr Asn Lys Phe Thr Asn Thr Ser Gly Phe Ala
1               5                   10                  15

Asn

<210> SEQ ID NO 19
<211> LENGTH: 16
<212> TYPE: PRT
<213> ORGANISM: Mus musculus

<400> SEQUENCE: 19

Pro Arg Leu Met Gly Lys Ile Leu Asp Val Lys Ser Asp Ala Gln Met
1               5                   10                  15

<210> SEQ ID NO 20
<211> LENGTH: 36
<212> TYPE: PRT
<213> ORGANISM: Artificial Sequence
<220> FEATURE:
<223> OTHER INFORMATION: fusion protein

<400> SEQUENCE: 20

```
Asn Ala Thr Pro Ile Thr Asn Lys Phe Thr Asn Thr Ser Gly Phe Ala
 1               5                  10                 15

Asn Glu Leu Gly Pro Arg Leu Met Gly Lys Ile Leu Asp Val Lys Ser
            20                  25                 30

Asp Ala Gln Met
        35

<210> SEQ ID NO 21
<211> LENGTH: 57
<212> TYPE: PRT
<213> ORGANISM: Artificial Sequence
<220> FEATURE:
<223> OTHER INFORMATION: fusion protein

<400> SEQUENCE: 21

Leu His Asn His His Thr Glu Lys Ser Leu Ser His Ser Pro Gly Lys
 1               5                  10                 15

Ala Ser Lys Leu Asn Ala Thr Pro Ile Thr Asn Lys Phe Thr Asn Thr
            20                  25                 30

Ser Gly Phe Ala Asn Glu Phe Ala Leu Ser Lys Thr Pro Asn Thr Glu
        35                  40                 45

Arg Gln Lys Glu Gln Glu Lys Ile Leu
        50                  55

<210> SEQ ID NO 22
<211> LENGTH: 57
<212> TYPE: PRT
<213> ORGANISM: Artificial Sequence
<220> FEATURE:
<223> OTHER INFORMATION: fusion protein

<400> SEQUENCE: 22

Leu His Asn His His Thr Glu Lys Ser Leu Ser His Ser Pro Gly Lys
 1               5                  10                 15

Ala Ser Lys Leu Asn Ala Thr Pro Ile Thr Asn Lys Phe Thr Asn Thr
            20                  25                 30

Ser Gly Phe Ala Asn Glu Leu Gly Pro Arg Leu Met Gly Lys Ile Leu
        35                  40                 45

Asp Val Lys Ser Asp Ala Gln Met Leu
        50                  55

<210> SEQ ID NO 23
<211> LENGTH: 54
<212> TYPE: PRT
<213> ORGANISM: Artificial Sequence
<220> FEATURE:
<223> OTHER INFORMATION: fusion protein

<400> SEQUENCE: 23

His Glu Gly Leu His Asn His His Thr Glu Lys Ser Leu Ser His Ser
 1               5                  10                 15

Pro Gly Lys Ala Ser Gly Phe Ala Asn Glu Leu Gly Pro Arg Leu Met
            20                  25                 30

Gly Lys Leu Thr Met Gly Ser Ile Gly Ala Ala Ser Met Glu Phe Cys
        35                  40                 45

Phe Asp Val Phe Lys Glu
        50

<210> SEQ ID NO 24
<211> LENGTH: 54
```

```
<212> TYPE: PRT
<213> ORGANISM: Artificial Sequence
<220> FEATURE:
<223> OTHER INFORMATION: fusion protein

<400> SEQUENCE: 24

Arg Pro Asn Ser Gly Ile Lys Cys Leu Ala Gly Cys Ser Gly His Ser
1               5                   10                  15

Gln Val Pro Thr Ser Gly Phe Ala Asn Glu Leu Gly Pro Arg Leu Met
            20                  25                  30

Gly Lys Leu Arg Ile Leu Gln Ser Thr Val Pro Arg Ala Arg Asp Pro
        35                  40                  45

Pro Val Ala Thr Met Val
    50

<210> SEQ ID NO 25
<211> LENGTH: 2264
<212> TYPE: DNA
<213> ORGANISM: Artificial Sequence
<220> FEATURE:
<223> OTHER INFORMATION: nucleic acid encoding a fusion protein

<400> SEQUENCE: 25
```

| | | | | | |
|---|---|---|---|---|---|
| atgggatggt | catgtatcat | ccttttttcta | gtagcaactg | caactggagt | acattcacag | 60 |
| gtgcagatcg | aattcgccct | tggtaagcct | atccctaacc | ctctcctcgg | tctcgattct | 120 |
| acgtctagtt | caggtaagtc | ctggacgcat | cccggctatg | cagtcccagt | ccagggcagc | 180 |
| aaggcaggcc | ccgtctgcct | cttcacccgg | aggcctctgc | cgcccccact | catgctcagg | 240 |
| gagagggtct | tctggctttt | ccccaggct | ctgggcaggc | acaggctagg | tgccctaac | 300 |
| ccaggccctg | cacacaaagg | ggcaggtgct | gggctcagac | ctgccaagag | ccatatccgg | 360 |
| gaggaccctg | cccctgacct | aagcccaccc | caaaggccaa | actctccact | ccctcagctc | 420 |
| ggacaccttc | tctcctccca | gattccagta | actcccaatc | ttctctctgc | agagcccaaa | 480 |
| tcttgtgaca | aaactcacac | atgcccaccg | tgcccaggta | agccagccca | ggcctcgccc | 540 |
| tccagctcaa | ggcgggacag | gtgccctaga | gtagcctgca | tccagggaca | ggccccagcc | 600 |
| gggtgctgac | acgtccacct | ccatctcttc | ctcagcacct | gaactcctgg | ggggaccgtc | 660 |
| agtcttcctc | ttcccccaa | aacccaagga | caccctcatg | atctcccgga | cccctgaggt | 720 |
| cacatgcgtg | gtggtggacg | tgagccacga | agaccctgag | gtcaagttca | actggtacgt | 780 |
| ggacggcgtg | gaggtgcata | atgccaagac | aaagccgcgg | gaggagcagt | acaacagcac | 840 |
| gtaccgtgtg | gtcagcgtcc | tcaccgtcct | gcaccaggac | tggctgaatg | caaggagta | 900 |
| caagtgcaag | gtctccaaca | aagccctccc | agccccatc | gagaaaacca | tctccaaagc | 960 |
| caaaggtggg | acccgtgggg | tgcgagggc | acatggacag | aggccggctc | ggcccaccct | 1020 |
| ctgccctgag | agtgaccgct | gtaccaacct | ctgtccctac | agggcagccc | cgagaaccac | 1080 |
| aggtgtacac | cctgccccca | tcccgggagg | agatgaccaa | gaaccaggtc | agcctgacct | 1140 |
| gcctggtcaa | aggcttctat | cccagcgaca | tcgccgtgga | gtgggagagc | aatgggcagc | 1200 |
| cggagaacaa | ctacaagacc | acgcctcccg | tgctggactc | cgacggctcc | ttcttcctct | 1260 |
| atagcaagct | caccgtggac | aagagcaggt | ggcagcaggg | gaacgtcttc | tcatgctccg | 1320 |
| tgatgcatga | ggctctgcac | aaccactaca | cgcagaagag | cctctccctg | tccccgggta | 1380 |
| aatccagctc | acaattgtct | agcaagctta | atgcaacacc | tatcacaaat | aagttcacaa | 1440 |
| acacgtccgg | ctttgcgaat | gaattgggac | ctaggttgat | gggcaaaata | ttggatgtga | 1500 |

```
agagtgatgc ccagatgttg aaaggtcgtg tggacaacat cagcaccctg ggttctgatc    1560
ttaagactga aagaggtcgt gtggacgatg ctgaggttca gatgcagata gtgaacacca    1620
ccctcaagag ggtgcgttct cagatcctgt ctttggaaac cagcatgaag atagccaatg    1680
atcagctcca gatattaaca atgagctggg gagaggttga cagtctcagt gccaaaatcc    1740
cagaactgaa aagagatctg ataaagcca gcgccttgaa cacaaaggtc caaggactac      1800
agaacagctt ggagaatgtc aacaagctgc tcaaacaaca gagtgacatt ctggagatgg    1860
tggctcgagg ctggaagtat ttctcgggga acttctatta cttttcacgc accccaaaga    1920
cctggtacag cgcagagcag ttctgtattt ctagaaaagc tcacctgacc tcagtgtcct    1980
cagaatcgga acaaaagttt ctctacaagg cagcagatgg aattccacac tggattggac    2040
ttaccaaagc agggagcgaa ggggactggt actgggtgga ccagacatca ttcaacaagg    2100
agcaaagtag gaggttctgg attccaggtg aacccaacaa cgcagggaac aatgagcact    2160
gtgccaatat cagggtgtct gccctgaagt gctggaacga tggtccctgt gacaatacat    2220
ttcttttcat ctgcaagagg ccctacgtcc aaacaactga atga                      2264

<210> SEQ ID NO 26
<211> LENGTH: 927
<212> TYPE: DNA
<213> ORGANISM: Artificial Sequence
<220> FEATURE:
<223> OTHER INFORMATION: nucleic acid encoding a fusion protein

<400> SEQUENCE: 26
atgtctgcac ttctgatcct agctcttgtt ggagctgcag ttgctgacta caaagacgat      60
gacgacaagc ttaatgcaac acctatcaca ataagttca caaacacgtc cggctttgcg      120
aatgaattgg gacctaggtt gatgggcaaa atattggatg tgaagagtga tgcccagatg      180
ttgaaaggtc gtgtggacaa catcagcacc ctgggttctg atcttaagac tgaaagaggt      240
cgtgtggacg atgctgaggt tcagatgcag atagtgaaca ccaccctcaa gagggtgcgt      300
tctcagatcc tgtctttgga aaccagcatg aagatagcca atgatcagct ccagatatta      360
acaatgagct ggggagaggt tgacagtctc agtgccaaaa tcccagaact gaaaagagat      420
ctggataaag ccagcgccct tgaacacaaa ggtccaagga cagaacag cttggagaat      480 gtcaacaagc tgctcaaaca acagagtgac attctggaga tggtggctcg aggctggaag      540
tatttctcgg ggaacttcta ttacttttca cgcacccaa agacctggta cagcgcagag      600
cagttctgta tttctagaaa agctcacctg acctcagtgt cctcagaatc ggaacaaaag      660
tttctctaca aggcagcaga tggaattcca cactggattg acttaccaa agcagggagc      720 gaagggact ggtactgggt ggaccagaca tcattcaaca aggagcaaag taggaggttc      780
tggattccag gtgaacccaa caacgcaggg aacaatgagc actgtgccaa tatcagggtg      840
tctgccctga gtgctggaa cgatggtccc tgtgacaata catttctttt catctgcaag      900
aggccctacg tccaaacaac tgaatga                                            927

<210> SEQ ID NO 27
<211> LENGTH: 76
<212> TYPE: PRT
<213> ORGANISM: Artificial Sequence
<220> FEATURE:
<223> OTHER INFORMATION: nucleic acid encoding OLLAS peptide

<400> SEQUENCE: 27

Ala Gly Ala Thr Cys Thr Ala Cys Cys Ala Thr Gly Ala Cys Thr Ala
```

```
              1               5                      10                     15
            Gly Thr Gly Gly Cys Thr Thr Thr Gly Cys Gly Ala Ala Thr Gly Ala
                               20                     25                     30
            Ala Thr Thr Gly Gly Gly Ala Cys Cys Thr Ala Gly Gly Thr Thr Gly
                        35                     40                     45
            Ala Thr Gly Gly Gly Cys Ala Ala Gly Cys Thr Thr Thr Cys Thr Ala
                   50                     55                     60
            Gly Ala Thr Ala Gly Cys Gly Gly Cys Cys Gly Cys
            65                     70                     75

<210> SEQ ID NO 28
<211> LENGTH: 1237
<212> TYPE: DNA
<213> ORGANISM: Artificial Sequence
<220> FEATURE:
<223> OTHER INFORMATION: nucleic acid encoding OLLAS-tagged ovalbumin

<400> SEQUENCE: 28
agatctacca tgactagtgg ctttgcgaat gaattgggac ctaggttgat gggcaagctt      60
accatgggct ccatcggcgc agcaagcatg gaatttgtt ttgatgtatt caaggagctc     120
aaagtccacc atgccaatga aacatcttc tactgcccca tgccatcat gtcagctcta     180 gccatggtat acctgggtgc aaaagacagc accaggacac aaataaataa ggttgttcgc     240
tttgataaac ttccaggatt cggagacagt attgaagctc agtgtggcac atctgtaaac     300
gttcactctt cacttagaga catcctcaac caaatcacca accaaatga tgtttattcc     360 ttcagccttg ccagtagact ttatgctgaa gagagatacc caatcctgcc agaatacttg     420
cagtgtgtga aggaactgta tagaggaggc ttggaaccta tcaactttca acagctgca     480 gatcaagcca gagagctcat caattcctgg gtagaaagtc agacaaatgg aattatcaga     540
aatgtccttc agccaagctc cgtggattct caaactgcaa tggttctggt taatgccatt     600
gtcttcaaag actgtggga aaaacatt aaggatgaag acacacaagc aatgcctttc     660
agagtgactg agcaagaaag caaacctgtg cagatgatgt accagattgg tttatttaga     720
gtggcatcaa tggcttctga aaaatgaag atcctggagc ttccatttgc cagtgggaca     780
atgagcatgt tggtgctgtt gcctgatgaa gtctcaggcc ttgagcagct tgagagtata     840
atcaactttg aaaaactgac tgaatggacc agttctaatg ttatgaaga gaggaagatc     900 aaagtgtact tacctcgcat gaagatggag gaaaaatacaa acctcacatc tgtcttaatg     960
gctatgggca ttactgacgt gtttagctct tcagccaatc tgtctggcat ctcctcagca    1020
gagagcctga agatatctca agctgtccat gcagcacatg cagaaatcaa tgaagcaggc    1080
agagaggtgg tagggtcagc agaggctgga gtggatgctg caagcgtctc tgaagaattt    1140
agggctgacc atccattcct cttctgtatc aagcacatcg caaccaacgc cgttctcttc    1200
tttggcagat gtgtttcccc ttctagatag cggccgc                            1237

<210> SEQ ID NO 29
<211> LENGTH: 887
<212> TYPE: DNA
<213> ORGANISM: Artificial Sequence
<220> FEATURE:
<223> OTHER INFORMATION: nucleic acid encoding FLAG-mLangerin.ECD

<400> SEQUENCE: 29
actagtacca tgtctgcact tctgatccta gctcttgttg gagctgcagt tgctgactac      60
aaagacgatg acgacaagct tggacctagg ttgatgggca aaatattgga tgtgaagagt     120
```

```
gatgcccaga tgttgaaagg tcgtgtggac aacatcagca ccctgggttc tgatcttaag      180
actgaaagag gtcgtgtgga cgatgctgag gttcagatgc agatagtgaa caccaccctc      240
aagagggtgc gttctcagat cctgtctttg gaaaccagca tgaagatagc caatgatcag      300
ctccagatat taacaatgag ctggggagag gttgacagtc tcagtgccaa atcccagaa      360 ctgaaaagag atctggataa agccagcgcc ttgaacacaa aggtccaagg actacagaac      420
agcttggaga atgtcaacaa gctgctcaaa caacagagtg acattctgga gatggtggct      480
cgaggctgga agtatttctc ggggaacttc tattactttt cacgcacccc aaagacctgg      540
tacagcgcag agcagttctg tatttctaga aagctcacc tgacctcagt gtcctcagaa        600
tcggaacaaa agtttctcta aaggcagca gatggaattc cacactggat tggacttacc        660
aaagcaggga gcgaagggga ctggtactgg gtggaccaga catcattcaa caaggagcaa      720
agtaggaggt tctggattcc aggtgaaccc aacaacgcag ggaacaatga gcactgtgcc      780
aatatcaggt gtctgccct gaagtgctgg aacgatggtc cctgtgacaa tacatttctt      840
ttcatctgca gaggcccta cgtccaaaca actgaatgag cggccgc                     887

<210> SEQ ID NO 30
<211> LENGTH: 902
<212> TYPE: DNA
<213> ORGANISM: Artificial Sequence
<220> FEATURE:
<223> OTHER INFORMATION: nucleic acid encoding FLAG-OFL/2-mLangerin.ECD

<400> SEQUENCE: 30
actagtacca tgtctgcact tctgatccta gctcttgttg gagctgcagt tgctgactac       60
aaagacgatg acgacaagct ttttgcgaat gaattgggac ctaggttgat gggcaaaata      120
ttggatgtga agagtgatgc ccagatgttg aaaggtcgtg tggacaacat cagcaccctg      180
ggttctgatc ttaagactga aagaggtcgt gtggacgatg ctgaggttca gatgcagata      240
gtgaacacca ccctcaagag ggtgcgttct cagatcctgt ctttggaaac cagcatgaag      300
atagccaatg atcagctcca gatattaaca atgagctggg gagaggttga cagtctcagt      360
gccaaaatcc cagaactgaa aagagatctg gataaagcca gcgccttgaa cacaaaggtc      420
caaggactac agaacagctt ggagaatgtc aacaagctgc tcaaacaaca gagtgacatt      480
ctggagatgg tggctcgagg ctggaagtat ttctcgggga acttctatta cttttcacgc      540
accccaaaga cctggtacag cgcagagcag ttctgtattt ctagaaaagc tcacctgacc      600
tcagtgtcct cagaatcgga acaaaagttt ctctacaagg cagcagatgg aattccacac      660
tggattggac ttaccaaagc agggagcgaa ggggactggt actgggtgga ccagacatca      720
ttcaacaagg agcaaagtag gaggttctgg attccaggtg aacccaacaa cgcagggaac      780
aatgagcact gtgccaatat cagggtgtct gccctgaagt gctggaacga tggtccctgt      840
gacaatacat ttcttttcat ctgcaagagg ccctacgtcc aaacaactga atgagcggcc      900
gc                                                                     902

<210> SEQ ID NO 31
<211> LENGTH: 841
<212> TYPE: DNA
<213> ORGANISM: Artificial Sequence
<220> FEATURE:
<223> OTHER INFORMATION: nucleic acid encoding FLAG-mSIGN-R1.ECD

<400> SEQUENCE: 31
```

```
actagtacca tgtctgcact tctgatccta gctcttgttg gagctgcagt tgctgactac      60
aaagacgatg acgacaagct ttccaaaacc ccaaataccg agaggcagaa ggaacaagag     120
aagatcctcc aggaactgac ccagctgaca gatgagctta cgtccaggat ccccatctcc     180
caagggaaga atgagtccat gcaggcgaag atcactgagc aactgatgca gctgaaaact     240
gaactcttgt ccaggattcc catcttccag gggcagaatg agtccataca agagaagatc     300
tctgagcaac tgatgcagct gaaggctgaa cttctttcca agatctccag cttcccggta     360
aaggatgatt ctaagcagga agatctctac caacagctgg tacagatgaa gactgaactc     420
ttccgcctgt gtcgactctg cccctgggac tggacattcc tcctaggaaa ttgttacttc     480
ttctccaagt cccagcggaa ctggaatgac gccgtcacag cttgcaaaga agtgaaggct     540
caactagtca tcatcaatag tgatgaagag cagaccttcc tgcagcagac ttctaaggct     600
aaaggaccaa cctggatggg cctgtcagac ctgaagaagg aggccacgtg gctctgggta     660
gatggttcta ctctgtcatc cagattccag aaatattgga atagagggga gcctaacaac     720
atcggtgagg aagactgtgt cgaatttgct ggggatggct ggaatgactc taaatgtgaa     780
ctcaaaaagt tctggatctg caagaagtct gcaaccccat gcactgaagg ctagcggccg     840
c                                                                     841

<210> SEQ ID NO 32
<211> LENGTH: 365
<212> TYPE: DNA
<213> ORGANISM: Artificial Sequence
<220> FEATURE:
<223> OTHER INFORMATION: nucleic acid encoding rat P11-FLAG.HA

<400> SEQUENCE: 32
gctagcacca ccatgccatc ccaaatggag catgccatgg aaaccatgat gcttacattt      60
cacaggtttg caggggaaaa aaactacttg acaaaggagg acctgagagt gctcatggaa     120
agggagttcc ctgggttttt ggaaaatcaa aaggaccctc tggctgtgga caaaataatg     180
aaagacctgg accagtgccg agatggaaaa gtgggcttcc agagctttct atcactagtg     240
gcggggctca tcattgcatg caatgactat tttgtagtac acatgaagca gaagaagacc     300
ggtgactaca aggacgacga tgacaagtac ccttatgacg tgcccgatta cgcttaagcg     360
gccgc                                                                 365

<210> SEQ ID NO 33
<211> LENGTH: 1484
<212> TYPE: DNA
<213> ORGANISM: Artificial Sequence
<220> FEATURE:
<223> OTHER INFORMATION: nucleic acid encoding human CD8.ECD-OFL-
      mLangerin.ECD

<400> SEQUENCE: 33
agatctacca tggccttacc agtgaccgcc ttgctcctgc cgctggcctt gctgctccac      60
gccgccaggc cgagccagtt ccgggtgtcg ccgctggatc ggacctggaa cctgggcgag     120
acagtggagc tgaagtgcca ggtgctgctg tccaacccga cgtcgggctg ctcgtggctc     180
ttccagccgc gcggcgccgc cgccagtccc accttcctcc tatacctctc ccaaaacaag     240
cccaaggcgg ccgaggggct ggacacccag cggttctcgg caagaggtt gggggacacc     300 ttcgtcctca cctgagcga cttccgccga gagaacgagg ctactatttt ctgctcggcc     360
ctgagcaact ccatcatgta cttcagccac ttcgtgccgg tcttcctgcc agcgaagccc     420
```

| | |
|---|---|
| accacgacgc cagcgccgcg accaccaaca ccggcgccca ccatcgcgtc gcagcccctg | 480 |
| tccctgcgcc cagaggcgtg ccggccagcg gcggggggcg cagtgcacac gaggggggctg | 540 |
| gacttcgcct gtgatcaatt cgcccttggt aagcctatcc ctaaccctct cctcggtctc | 600 |
| gattctacgt ctagcaagct taatgcaaca cctatcacaa ataagttcac aaacacgtcc | 660 |
| ggctttgcga atgaattggg acctaggttg atgggcaaaa tattggatgt gaagagtgat | 720 |
| gcccagatgt tgaaaggtcg tgtggacaac atcagcaccc tgggttctga tcttaagact | 780 |
| gaaagaggtc gtgtggacga tgctgaggtt cagatgcaga tagtgaacac caccctcaag | 840 |
| agggtgcgtt ctcagatcct gtctttggaa accagcatga agatagccaa tgatcagctc | 900 |
| cagatattaa caatgagctg gggagaggtt gacagtctca gtgccaaaat cccagaactg | 960 |
| aaaagagatc tggataaagc cagcgccttg aacacaaagg tccaaggact acagaacagc | 1020 |
| ttggagaatg tcaacaagct gctcaaacaa cagagtgaca ttctggagat ggtggctcga | 1080 |
| ggctggaagt atttctcggg gaacttctat tacttttcac gcaccccaaa gacctggtac | 1140 |
| agcgcagagc agttctgtat ttctagaaaa gctcacctga cctcagtgtc ctcagaatcg | 1200 |
| gaacaaaagt ttctctacaa ggcagcagat ggaattccac actggattgg acttaccaaa | 1260 |
| gcagggagcg aaggggactg gtactgggtg accagacat cattcaacaa ggagcaaagt | 1320 |
| aggaggttct ggattccagg tgaacccaac aacgcaggga caatgagca ctgtgccaat | 1380 |
| atcagggtgt ctgccctgaa gtgctggaac gatggtccct gtgacaatac atttcttttc | 1440 |
| atctgcaaga ggccctacgt ccaaacaact gaatgagcgg ccgc | 1484 |

<210> SEQ ID NO 34
<211> LENGTH: 716
<212> TYPE: DNA
<213> ORGANISM: Artificial Sequence
<220> FEATURE:
<223> OTHER INFORMATION: nucleic acid encoding hCD8.ECD-OFL-mLangerin.
ECD.deletion.#1

<400> SEQUENCE: 34

| | |
|---|---|
| agatctacca tggccttacc agtgaccgcc ttgctcctgc cgctggcctt gctgctccac | 60 |
| gccgccaggc cgagccagtt ccgggtgtcg ccgctggatc ggacctggaa cctgggcgag | 120 |
| acagtggagc tgaagtgcca ggtgctgctg tccaacccga cgtcgggctg ctcgtggctc | 180 |
| ttccagccgc gcggcgccgc cgccagtccc accttcctcc tatacctctc ccaaaacaag | 240 |
| cccaaggcgg ccgaggggct ggacacccag cggttctcgg gcaagaggtt gggggacacc | 300 |
| ttcgtcctca ccctgagcga cttccgccga gagaacgagg gctactattt ctgctcggcc | 360 |
| ctgagcaact ccatcatgta cttcagccac ttcgtgccgg tcttcctgcc agcgaagccc | 420 |
| accacgacgc cagcgccgcg accaccaaca ccggcgccca ccatcgcgtc gcagcccctg | 480 |
| tccctgcgcc cagaggcgtg ccggccagcg gcggggggcg cagtgcacac gaggggggctg | 540 |
| gacttcgcct gtgatcaatt cgcccttggt aagcctatcc ctaaccctct cctcggtctc | 600 |
| gattctacgt ctagcaagct taatgcaaca cctatcacaa ataagttcac aaacacgtcc | 660 |
| ggctttgcga atgaattggg acctaggttg atgggcaaaa tattgtgagc ggccgc | 716 |

<210> SEQ ID NO 35
<211> LENGTH: 701
<212> TYPE: DNA
<213> ORGANISM: Artificial Sequence
<220> FEATURE:
<223> OTHER INFORMATION: nucleic acid encoding hCD8.ECD-OFL-mLangerin.
ECD.deletion.#2

<400> SEQUENCE: 35

```
agatctacca tggccttacc agtgaccgcc ttgctcctgc cgctggcctt gctgctccac    60
gccgccaggc cgagccagtt ccgggtgtcg ccgctggatc ggacctggaa cctgggcgag   120
acagtggagc tgaagtgcca ggtgctgctg tccaacccga cgtcgggctg ctcgtggctc   180
ttccagccgc gcggcgccgc cgccagtccc accttcctcc tatacctctc ccaaaacaag   240
cccaaggcgg ccgaggggct ggacacccag cggttctcgg caagaggtt ggggacacc    300
ttcgtcctca ccctgagcga cttccgccga gagaacgagg ctactatttt ctgctcggcc   360
ctgagcaact ccatcatgta cttcagccac ttcgtgccgg tcttcctgcc agcgaagccc   420
accacgacgc cagcgccgcg accaccaaca ccggcgccca ccatcgcgtc gcagcccctg   480
tccctgcgcc cagaggcgtg ccggccagcg cgggggggcg cagtgcacac gagggggctg   540
gacttcgcct gtgatcaatt cgcccttggt aagcctatcc ctaaccctct cctcggtctc   600
gattctacgt ctagcaagct taatgcaaca cctatcacaa ataagttcac aaacacgtcc   660
ggctttgcga atgaattggg acctaggttg tgagcggccg c                      701
```

<210> SEQ ID NO 36
<211> LENGTH: 883
<212> TYPE: DNA
<213> ORGANISM: Artificial Sequence
<220> FEATURE:
<223> OTHER INFORMATION: nucleic acid encoding OT1-EGFP-OLLAS

<400> SEQUENCE: 36

```
agatctacca tggatgaagt ctcaggcctt gagcagcttg agagtataat caactttgaa    60
aaactgactg aatggaccag ttctaatgtt atggaattgg tgagcaaggg cgaggagctg   120
ttcaccgggg tggtgcccat cctggtcgag ctggacggcg acgtaaacgg ccacaagttc   180
agcgtgtccg gcgagggcga gggcgatgcc acctacggca agctgaccct gaagttcatc   240
tgcaccaccg gcaagctgcc cgtgccctgg cccaccctcg tgaccaccct gacctacggc   300
gtgcagtgct tcagccgcta ccccgaccac atgaagcagc acgacttctt caagtccgcc   360
atgcccgaag gctacgtcca ggagcgcacc atcttcttca aggacgacgg caactacaag   420
acccgcgccg aggtgaagtt cgagggcgac accctggtga accgcatcga gctgaagggc   480
atcgacttca aggaggacgg caacatcctg ggcacaagc tggagtacaa ctacaacagc   540
cacaacgtct atatcatggc cgacaagcag aagaacggca tcaaggtgaa cttcaagatc   600
cgccacaaca tcgaggacgg cagcgtgcag ctcgccgacc actaccagca gaacacccc    660
atcggcgacg gccccgtgct gctgcccgac aaccactacc tgagcaccca gtccgccctg   720
agcaaagacc ccaacgagaa gcgcgatcac atggtcctgc tggagttcgt gaccgccgcc   780
gggatcactc tcggcatgga cgagctgtac aagtccggag ctagtggctt gcgaatgaa   840
ttgggaccta ggttgatggg caagctttct agatagcggc cgc                    883
```

<210> SEQ ID NO 37
<211> LENGTH: 843
<212> TYPE: DNA
<213> ORGANISM: Artificial Sequence
<220> FEATURE:
<223> OTHER INFORMATION: nucleic acid encoding FLAG.OLLAS-EGFP

<400> SEQUENCE: 37

```
agatctacca tggactacaa agacgatgac gacaagcttg gcactagtgg ctttgcgaat    60
```

```
gaattgggac ctaggttgat gggcaagctt tctagtcaat tggtgagcaa gggcgaggag      120
ctgttcaccg gggtggtgcc catcctggtc gagctggacg gcgacgtaaa cggccacaag      180
ttcagcgtgt ccggcgaggg cgagggcgat gccacctacg gcaagctgac cctgaagttc      240
atctgcacca ccggcaagct gcccgtgccc tggcccaccc tcgtgaccac cctgacctac      300
ggcgtgcagt gcttcagccg ctaccccgac cacatgaagc agcacgactt cttcaagtcc      360
gccatgcccg aaggctacgt ccaggagcgc accatcttct tcaaggacga cggcaactac      420
aagacccgcg ccgaggtgaa gttcgagggc gacaccctgg tgaaccgcat cgagctgaag      480
ggcatcgact tcaaggagga cggcaacatc ctggggcaca gctggagta caactacaac       540 agccacaacg tctatatcat ggccgacaag cagaagaacg gcatcaaggt gaacttcaag      600
atccgccaca acatcgagga cggcagcgtg cagctcgccg accactacca gcagaacacc      660
cccatcggcg acggccccgt gctgctgccc gacaaccact acctgagcac ccagtccgcc      720
ctgagcaaag accccaacga gaagcgcgat cacatggtcc tgctggagtt cgtgaccgcc      780
gccgggatca ctctcggcat ggacgagctg tacaagtccg gagctagcaa gctttgaact      840
agt                                                                    843

<210> SEQ ID NO 38
<211> LENGTH: 232
<212> TYPE: DNA
<213> ORGANISM: Artificial Sequence
<220> FEATURE:
<223> OTHER INFORMATION: nucleic acid encoding mSIGN-R1.Cytosol-OLLAS

<400> SEQUENCE: 38
agatctacca tgagtgactc cacagaagcc aagatgcagc ctcttagctc catggacgat       60
gatgagttga tggtcagcgg cagcaggtat tctattaaaa gctccagact acgaccaaat      120
tctggaatca agtgtttggc aggatgctcg ggacacagcc aagtccccac tagtggcttt      180
gcgaatgaat tgggacctag gttgatgggc aagctttcta gatagcggcc gc              232
```